(12) United States Patent
Tokito et al.

(10) Patent No.: US 6,416,887 B1
(45) Date of Patent: Jul. 9, 2002

(54) ORGANIC ELECTROLUMINESCENT ELEMENT

(75) Inventors: Shizuo Tokito; Koji Noda; Hisayoshi Fujikawa; Masahiko Ishii; Yasunori Taga; Makoto Kimura; Yasuhiko Sawaki, all of Aichi (JP)

(73) Assignee: Kabushiki Kaisha Toyota Chuo Kenkyusho, Aichi-gun (JP)

( * ) Notice: Subject to any disclaimer, the term of this patent is extended or adjusted under 35 U.S.C. 154(b) by 0 days.

(21) Appl. No.: 09/581,544

(22) PCT Filed: Nov. 11, 1999

(86) PCT No.: PCT/JP99/06290

§ 371 (c)(1),
(2), (4) Date: Jul. 11, 2000

(87) PCT Pub. No.: WO00/27946

PCT Pub. Date: May 18, 2000

(30) Foreign Application Priority Data

Nov. 11, 1998 (JP) .............................. 10-321080
Nov. 3, 1999 (JP) .......................... 11-065683

(51) Int. Cl.$^7$ .............................. H05B 33/14
(52) U.S. Cl. .................. 428/690; 428/917; 428/704; 313/504; 313/506
(58) Field of Search ................. 428/690, 704, 428/917; 313/504, 506

(56) References Cited

U.S. PATENT DOCUMENTS 5,773,929 A * 6/1998 Shi et al. .................... 313/504

FOREIGN PATENT DOCUMENTS

| EP | 676461 | 7/1997 | | |
|---|---|---|---|---|
| JP | 7-286170 | 10/1995 | | |
| JP | 10-168443 | 6/1998 | | |
| JP | 11-54284 | 2/1999 | | |
| JP | 1154284 A | * 2/1999 | ........... | H05B/33/14 |
| JP | 11-273863 | 10/1999 | | |
| WO | WO 96/17035 | 6/1996 | | |

* cited by examiner

Primary Examiner—Cynthia H. Kelly
Assistant Examiner—Ling Xu
(74) Attorney, Agent, or Firm—Oblon, Spivak, McClelland, Maier & Neustadt, P.C.

(57) ABSTRACT

An organic EL element has an anode, a cathode, and one or more organic compound layers sandwiched between the anode and cathode, wherein at least one layer of said organic compound layers includes an organic compound denoted by chemical formula (1), which is more specifically denoted by chemical formulas (2)–(5). By introducing desired substituents at $R_1$–$R_4$, these compounds can be made to demonstrate hole transport function, emissive function, electron transport function, or a combination of those functions. Due to its tendency to be structurally non-planar, the organic compound does not crystallize easily, and has a high glass transition temperature. Use of such a compound in an organic EL element enhances element life.

(a)

(b)

(c)

(d)

-continued
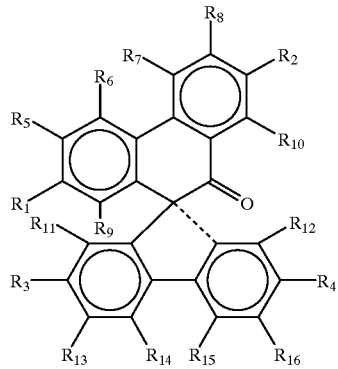
(2)
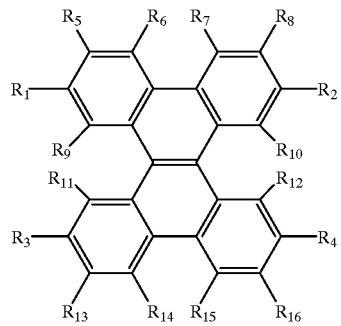
(3)
-continued
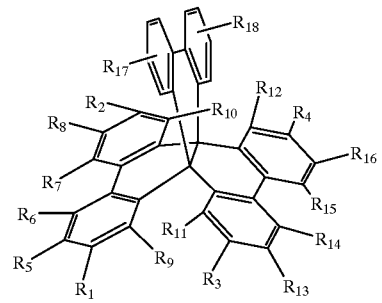
(4)
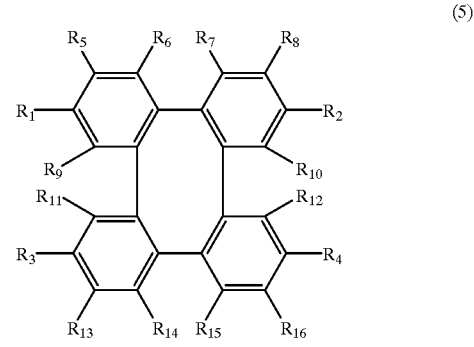
(5)
8 Claims, 8 Drawing Sheets

ORGANIC ELECTROLUMINESCENT ELEMENT

TECHNICAL FIELD

The present invention relates to an organic electroluminescence element (hereinafter referred to as an organic EL element), and more particularly relates to the material of its organic compound layer.

BACKGROUND ART

The recent rapid development in information media has created a large demand for display device innovation to enable rapid and precise conveyance of as much information as possible. In this present-day situation, self-emissive organic EL elements, which possess features such as high-speed response, high luminance, low power consumption, and reduced occupying space, have gained attention for use as elements in next generation flat panel displays and planar light sources, and much research has been directed to organic EL elements.

An organic EL element using organic compounds in its emissive layer is characterized in that it can emit light of a high luminance. By applying a direct current of several volts to a thin film element composed of a metal cathode and a fluorescent organic layer having a thickness of only about 100 nm formed on a transparent anode, a large current close to 1 $A/cm^2$ can be made to flow in the element. Efforts are being made to put such elements to practical use.

However, organic EL elements have not yet achieved sufficient stability and durability. Improvements in these points are indispensable for competing with of other types of displays.

It is known that the stability of the film structure of the organic thin film constituting the organic EL element significantly relates to the stability and durability of the element as a whole. In general, it is desirable that the organic thin film be made of a material that can be formed in an amorphous state and can maintain its amorphous state in a stable manner. However, crystallization begins to occur in an organic compound from the amorphous state when the glass transition temperature Tg is exceeded. Molecular movement is then activated, and the organic compound becomes unstable. Accordingly, to obtain a more stable organic thin film, it is necessary to develop a material having a high glass transition temperature Tg in addition to a high melting point Tm, and excellent heat resistance.

Four examples shown in FIG. 1 are representative configurations of the presently known organic EL elements. The optimal element configuration for the organic compound layer between a cathode and an anode differs depending on the characteristics of the employed organic material. For example, in the element of FIG. 1(a), a single emissive layer (EML) is disposed between a cathode and an anode, and this emissive layer also serves the functions of an electron transport layer (ETL) and a hole transport layer (HTL). In the element of FIG. 1(b), the emissive layer simultaneously serves as the electron transport layer. The hole transport layer supplies holes into the emissive layer to generate light emission. In the element of FIG. 1(c), the cathode supplies electrons to the electron transport layer. The anode supplies holes to the emissive layer which also functions as the hole transport layer. Light emission is generated near the interface between the emissive layer and the electron transport layer. In the element of FIG. 1(d), electrons are supplied to the emissive layer from the electron transport layer, and holes from the hole transport layer. The electrons and the holes recombine within the emissive layer to emit light. Presently, appropriate organic compounds are being proposed for the organic layers of elements having these various configurations.

The organic compound layer constituting the organic thin film is composed using, as referenced to above, a compound having hole transport function, a compound having electron transport function, and a compound having emissive function. Though it is desirable that one compound possess all of these characteristics (see FIG. 1(a)), usually a plurality of compounds are overlapped to form the organic compound layer (see FIG. 1(b)–(d)).

A representative hole transport material is an aromatic amine compound. Especially, dimer of triphenylamine, TPD (triphenylamine dimer), is known as an exemplary hole transport material. TPD can be easily formed on a substrate as a uniform amorphous thin film by vacuum deposition. However, there is a problem with TPD in that its glass transition temperature Tg is low, at 60° C., and that TPD crystallizes even at room temperature after a long time, changing into an irregular film. Such a change in the film structure resulting from crystallization directly influences the life of EL elements. Provision of a hole transport material capable of maintaining a stable film configuration and having high glass transition temperature Tg is for this reason desired.

The same can be written about electron transport materials. Compounds including oxadiazole (PBD, BND) and triazole (TAZ) structures are known as electron transport materials. However, many of these materials also have low glass transition temperatures Tg and tend to crystallize. It is therefore difficult to achieve a stable element when these materials are used as the electron transport materials. Other problems of these materials, such as the requirement for a high drive voltage and insufficient durability, have also been pointed out.

Methods are recently proposed for raising the Tg of materials constituting an organic thin film. Such methods include introducing branches and non-planarity in the compound molecular structure to reduce intermolecular aggregation strength, thereby suppressing crystallizing property. Increasing the molecular weight is another of such methods. Polymers having starburst, Spiro, or linear structures, for example, are representative compounds obtained by those methods. A Spiro structure especially creates an extremely non-planar molecular structure, and use of this structure allows development of materials having high heat resistance. The Spiro compounds of tryphenylamine, oxadiazole, and oligophenylene, for example, can be hole transport, electron transport, and emissive materials, respectively.

Recently, a compound integrating spiro structure, in which branches and non-planarity are introduced into the molecular structure to reduce intermolecular aggregation strength and to thereby decrease crystallization property was presented by Hoechst (Polymer Preprints 38 (1997) 349). The compound presented here has the configuration denoted by the chemical formula below wherein two identical structural units are bonded, and demonstrates only one type of property.

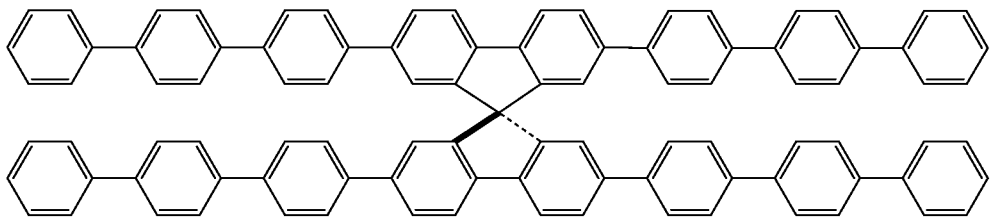

The above Spiro compound shows excellent structural stability, but lacks flexibility (allows for little variety) in its molecular structure. Moreover, this material is insufficient in terms of its electronic property. When the basic unit of the material has electron transport property, the material only demonstrates electron transport property. The material only functions as an emissive material when the basic unit is emissive. It is therefore necessary to separately develop new compounds exclusively for each of the properties.

DISCLOSURE OF THE INVENTION

The present invention was created in the above light. The object of the present invention is to provide a new organic material having high heat resistance, into which properties such as electron transport property, hole transport property, and emissive property can be freely integrated as the property of the organic compound.

The electroluminescence element of the present invention is an organic EL element having an anode, a cathode, and one or more organic compound layers sandwiched between the anode and cathode, wherein at least one layer of the organic compound layers includes an organic compound having the structure in which two biphenyl derivatives are bonded, as denoted by chemical formula (1).

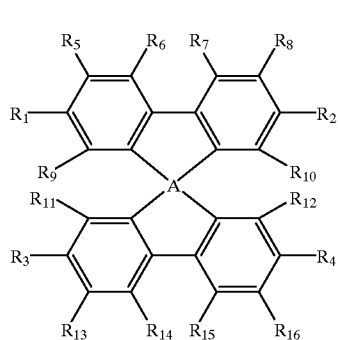

(1)

However, in the present invention, the above [A] does not include a structure composed of only a single carbon atom. In other words, the compound of chemical formula (1) does not include the structure in which two biphenyl derivatives are directly bonded in a Spiro bond. Specifically, the above [A] includes (i) two or more carbon atoms, (ii) a combination of one or more carbon atoms and a desired substituent or atom other than carbon, or (iii) a structure in which two biphenyl derivatives directly link at a plurality of sites without a bridging atom. In an organic compound having such a structure, adjacent substituents of the two biphenyl derivatives interfere with one another and generate steric hindrance. Accordingly, the two biphenyl derivatives do not locate themselves on one plane, and generate a twisted non-planar structure. Alternatively, while the two biphenyl derivatives are located within one plane, the substituents are positioned in a structure twisted from the plane. As a result, intermolecular aggregation strength can be reduced, providing a highly stable compound having reduced crystallizing property, a high glass transition temperature, and a high melting point.

Further, the organic EL element according to the present invention may include in at least one of the organic compound layers an organic compound given by the following chemical formula (2)

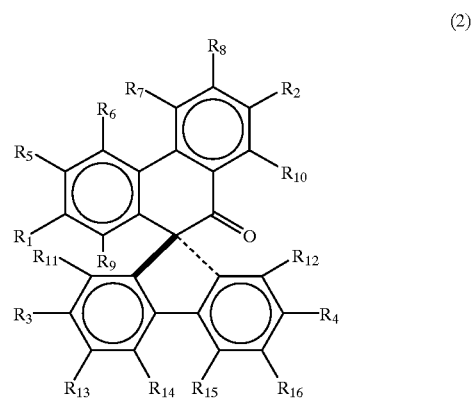

(2)

which can be described as the above chemical formula (1) having a bond formed at [A] via ketone (carbonyl group).

The compound of the above chemical formula (2) is a spiro compound having asymmetrical basic skeletons. One of the basic skeletons constituting the asymmetrical Spiro compound is a fluorene skeleton, while the pairing skeleton comprises a molecular structure other than fluorene skeleton, thereby forming an a symmetrical spiro structure. According to this spiro structure having asymmetrical basic skeletons, the compound of chemical formula (2) can be easily used as a variety of organic materials for electroluminescence elements by replacing desired groups in chemical formula (2) ($R_1$–$R_4$, for example) with substituents appropriate for the usage of the material.

In addition, the chemical substance of chemical formula (2) has a molecular structure into which branches and non-planarity are introduced to reduce intermolecular aggregation strength and to thereby decrease crystallization property, and is a stable compound with high glass transition temperature.

Still further, the skeleton of the structure pairing with the fluorene skeleton in chemical formula (2) may include cyclohexanone. When such a compound is employed in the organic material layer of an organic electroluminescence element, the presence of carbonyl group in cyclohexanone enhances the adhesion property of the organic material layer with respect to the transparent electrode, made of ITO (indium tin oxide), for example, used as an electrode, allowing improvement of element durability.

According to another aspect of the present invention, at least one of the organic compound layers of the organic EL element includes an organic compound expressed by the following chemical formula (3).

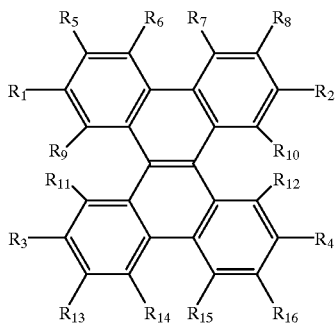

(3)

The compound of chemical formula (3) has a structure in which [A] of the above-mentioned chemical formula (1) is a double bond and the two biphenyl derivatives are bonded via this double bond.

The compound of chemical formula (3) is configured to include a widely extended and developed conjugated system. In such a compound having a developed conjugated system, π electron system extends in the entire molecule. Accordingly, high emission efficiency can be accomplished, and excellent performance can be expected with regards to hole transport and electron transport functions.

Another feature of the present invention is that at least one of the organic compound layers of the organic EL element may include an organic compound expressed by the following chemical formula (4).

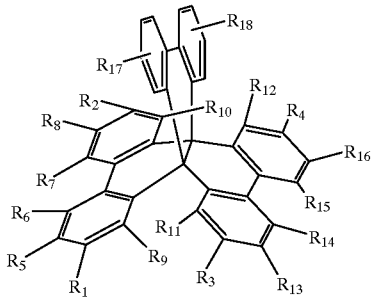

(4)

The compound of chemical formula (4) has a structure in which [A] of the above-mentioned chemical formula (1) includes a third biphenyl (which may be its derivative), providing a three-dimensional structure. The compound therefore has an extremely high glass transition temperature Tg. By using this compound, it is possible to achieve a stable organic compound layer which is unlikely to crystallize even when formed into a thin film.

A further feature of the present invention is that an organic compound expressed by chemical formula (1), or more specifically, by any one of chemical formulas (2), (3), and (4), can be used as an emissive layer material having hole transport function.

According to the present invention, by introducing desired substituents in $R_1$–$R_4$, for example, an organic compound simultaneously having hole transport function and extremely high emission efficiency can be obtained. Such an organic compound having hole transport and emissive functions may be used to form, together with an electron transport layer, an organic compound layer of an organic EL element in a two-layer configuration. In such a two-layer configuration, due to the presence of the electron transport layer between the emissive layer and the cathode, excitons generated by the recombining of electrons and holes within the emissive layer are less likely move through the electron transport layer to reach the cathode. This in turn prevents excitons from being lost at the interface with the cathode without contributing to light emission. Accordingly, higher emission efficiency can be achieved in this configuration compared to a case when light emission is performed in an emissive layer that also serves as the electron transport layer.

In the above chemical formulas (1)–(4), substituents having desired properties can be introduced as substituents $R_1$–$R_{16}$ (additionally as $R_{17}$ and $R_{18}$ in chemical formula (4)), and especially in $R_1$–$R_4$, to allow a single organic compound to possess a plurality of functions such as hole transport and emissive functions as described above, or electron transport and emissive functions.

A still further feature of the present invention is that the organic compound expressed by any one of chemical formulas (1)–(4) may be used as a host material within an emissive layer constituted by injecting a doping material within the host material.

The compound can be used as the host material of an emissive layer, as mentioned above, through selection of substituents $R_1$–$R_4$ to be introduced. Appropriate selection of materials allows adjustment of emitted color and improvement in emission efficiency, resulting in high efficiency organic EL elements capable of emitting light with a high luminance.

According to another aspect of the present invention, an organic EL element comprises a first emissive layer including, as an emissive material, an organic compound expressed by any of the above chemical formulas (1) to (4), and a second emissive layer including a material different from the material of the first emissive layer, wherein combined light including light from the first emissive layer and light from the second emissive layer is used as the light emitted by the element.

By allowing light from the first and the second emissive layers to coexist as mentioned above, a desired mixed color can be achieved. For example, white light emission may be generated employing the organic compound of the present invention and another compound.

A further feature of the present invention is that at least one of the organic compound layers of the organic EL element may include an organic compound expressed by the following chemical formula (5).

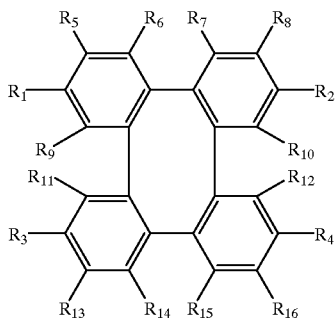

(5)

The compound of chemical formula (5) comprises an orthotetraphenylene skeleton, which can be described as the above chemical formula (1) having no atom in [A], in which two biphenyl derivatives are directly bonded to one another in a plurality of sites (two sites).

A still further feature of the present invention is that the organic compound expressed by chemical formula (5) may be used as a hole transport layer material for transporting holes from the anode to the emissive layer.

In the compound of the present invention expressed by chemical formula (5), groups having desired properties can be introduced especially as substituents $R_1$, $R_2$, $R_3$, and $R_4$ among the plurality of substituents $R_1$–$R_{16}$, to allow the compound to possess hole transport property, emissive property, or electron transport property. Moreover, a plurality of properties, such as the emissive property and hole transport property, can be imparted to the compound. Accordingly, this compound can easily be used as organic material for a variety of organic EL elements.

While example combinations shown in Table 1 described later can be applied to the substituents $R_1$, $R_2$, $R_3$, and $R_4$ in the compounds of the present invention expressed by the above chemical formulas (1)–(5), each of the substituents may be selected from hydrogen, alkyl group, alkoxy group, phenyl group, substituted phenyl group, diphenylamino group, diarylamino group, and other groups such as heterocyclic group and substituted heterocyclic group. No particular restrictions exist for other substituents $R_5$–$R_{16}$ in chemical formulas (1)–(5) (additionally for $R_{17}$ and $R_{18}$ in chemical formula (4)).

In the organic compounds expressed by chemical formulas (1)–(3) and (5), the two biphenyl derivatives generate steric hindrance due to the presence of the substituents $R_9$ and $R_{11}$, and $R_{10}$ and $R_{12}$ (in the organic compound of chemical formula (2), the steric hindrance is mostly due to the closely located $R_9$ and $R_{11}$). The two biphenyl derivatives are therefore prevented from being located within one plane. In addition, $R_{14}$ and $R_{15}$, and $R_6$ and $R_7$ also generate steric hindrance. In this way, the organic compounds expressed by chemical formulas (1)–(3) and (5) possess a twisted non-planar structure. This non-planar structure reduces intermolecular aggregation strength, thereby decreasing crystallizing property. Further, high glass transition temperature Tg and high melting point Tm are achieved, providing stable compounds having excellent heat resistance. Accordingly, stability of the organic layer can be enhanced by using these organic compounds, either alone or in combination with other organic compound materials, as the material for the organic layer. Furthermore, the organic compound of chemical formula (4) having a three-dimensional structure as described above is non-planar and has high heat stability without depending on $R_1$–$R_{16}$, $R_{17}$, and $R_{18}$.

DESCRIPTION OF REFERENCE NUMERALS

Figure 1:
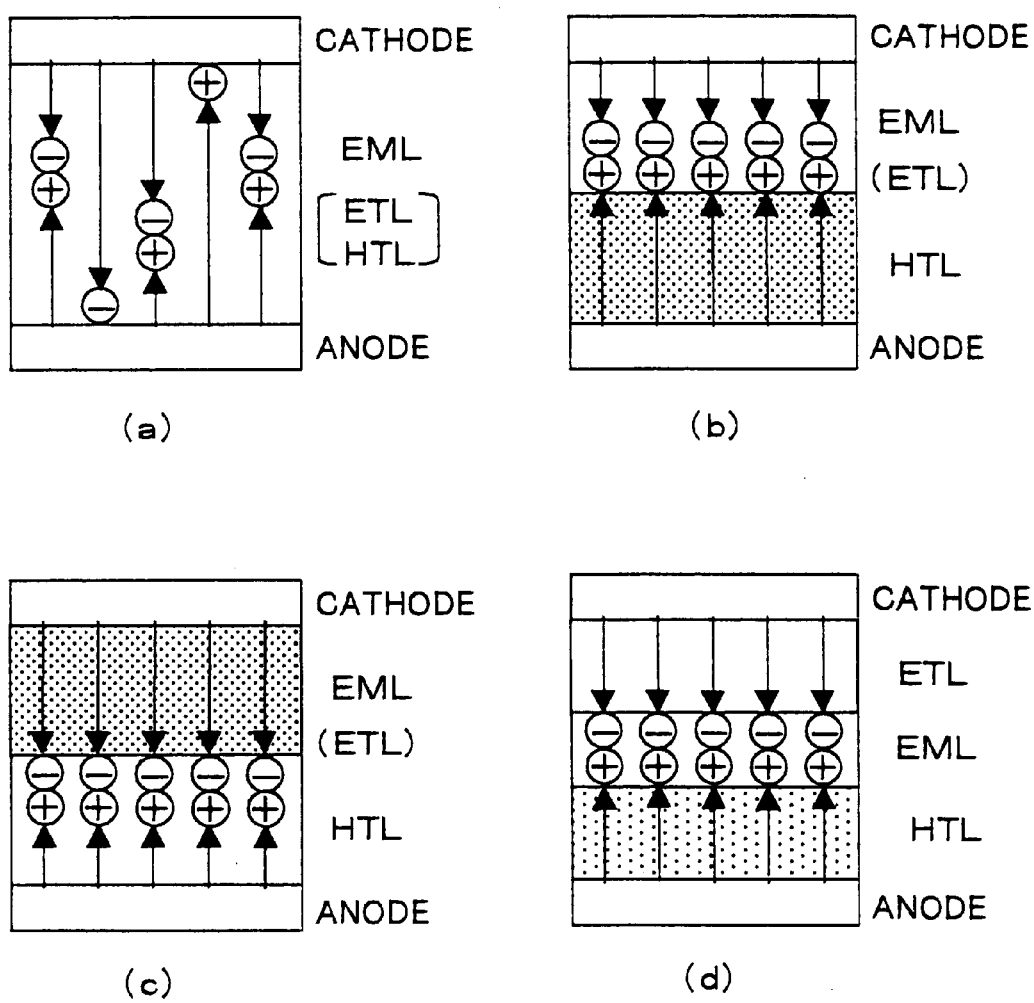
FIGS. 1(a), (b), (c), and (d) are diagrams showing representative configurations of an organic EL element.

10 transparent substrate (glass substrate), 12 transparent electrode (ITO, anode), 18 metal electrode (cathode), 20 organic compound layer, 22 hole transport layer, 24 emissive layer, 30 first emissive layer, 32 Alq$_3$ layer, 34 second emissive layer, 36 electron transport layer.

BEST MODES FOR CARRYING OUT THE INVENTION

The preferred embodiments of the present invention (hereinafter referred to as embodiments) will be described while referring to the drawings.

Figure 2:
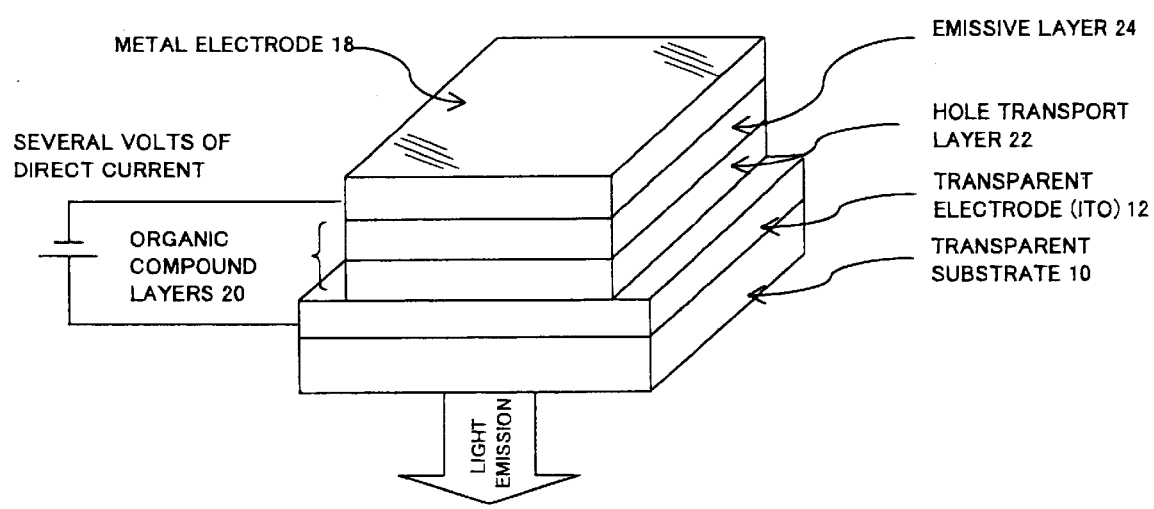
FIG. 2 is a diagram showing a configuration of an organic EL element using an organic compound layer of the present invention.

An organic EL element according to an embodiment of the present invention emits light based on the principle illustrated in FIGS. 1(a)–(d) described above, and has a basic structure as shown in the example of FIG. 2.

In FIG. 2, the organic EL element is constituted by overlapping on a transparent substrate 10, in order, a first electrode 12, an organic compound layer 20 which emits light by applying an electric field, and a second electrode 18.

Substrates such as a glass substrate, a transparent ceramic substrate, and a diamond substrate may be employed as the transparent substrate 10. As the first electrode 12, a transparent electrode having high light transmission and conductivity is employed. This electrode may be made of a thin film material such as ITO (indium tin oxide), $SnO_2$, $In_2O_3$, and polyaniline.

The organic compound layer 20 can be configured in, for example, a single-layer structure comprising an emissive layer, a two-layer structure comprising a hole transport layer and an emissive layer, or a three-layer structure comprising a hole transport layer, an emissive layer, and an electron transport layer. In this way, the organic compound layer 20 may either have a single-layer or multi-layer structure. The thickness of the organic compound layer 20 may be about several ten to several hundred nm. In the example of FIG. 2, the organic compound layer 20 comprises a two-layer structure including the hole transport layer 22 and the emissive layer 24.

In the present invention, at least one layer within the organic compound layer 20 uses an organic compound expressed by chemical formula (1).

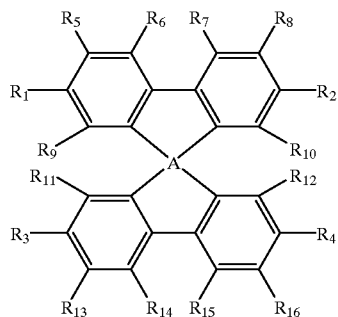

(1)

More specifically, the organic compound of chemical formula (1) can be expressed by chemical formulas (2)–(5) related to the embodiments of the present invention described below.

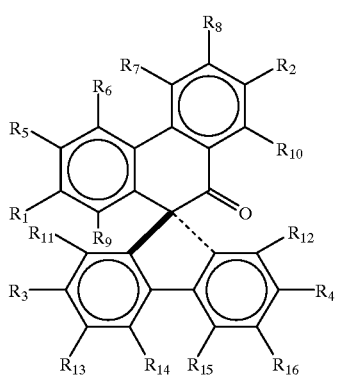

(2)

-continued

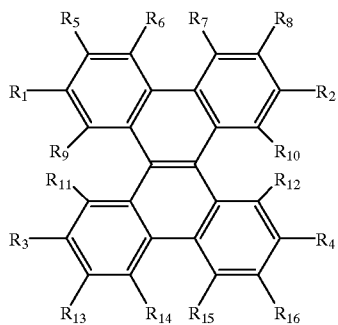

(3)

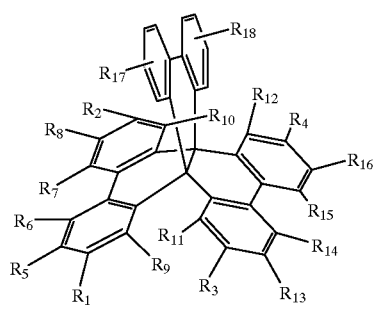

(4)

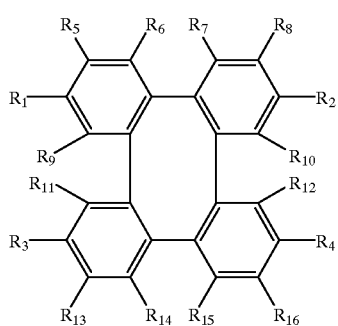

(5)

These organic compounds are used in at least a portion of the organic compound layer 20 as an emissive material, doping material, hole transport material, electron transport material, or, for example, an emissive material that simultaneously functions as a hole transport material. Materials which can be used in the organic compound layer 20 in combination with an organic compound of the present invention are molecules having electron transport function, molecules having emissive function, molecules having hole transport function, matrixes, binders, or other molecules having a plurality of these functions, which are conventionally known. The organic compound layer 20 including the organic compound of the present invention in the hole transport layer, the emissive layer, or the electron transport layer can be deposited by vacuum deposition, or formed into a film from a solution.

The second electrode 18 formed on the organic compound layer 20 is typically formed using a metal such as Mg, Ag, Ca, Li, Al, and In, or an alloy of those metals. A very thin layer of a fluoride or an oxide of an alkali metal or alkaline earth metal may be disposed between the metal layer serving as the cathode and the organic compound layer, so as to, together with the metal layer, form a multi-layer metal electrode.

In an organic EL element having such an arrangement, the transparent electrode 12 is used as the anode, and the metal electrode 18 as the cathode. Holes and electrons are injected from these electrodes into the organic compound layer 20, The injected holes and electrons recombine within the organic compound layer 20 which includes the organic compound of the present invention, thereby generating light emission.

[Description of the Organic Compound Expressed by Chemical Formula (1)]

Structure A

[A] of the above chemical formula (1) includes no structure composed only of a single carbon atom. In other words, the compound of chemical formula (1) does not include the structure in which two biphenyl derivatives are directly bonded in a spiro bond. Specifically, the above [A] includes (i) two or more carbon atoms, (ii) a combination of one or more carbon atoms and a desired substituent or atom other than carbon, or (iii) no atom such that two biphenyl derivatives directly link at a plurality of sites.

When [A] is a single bond of carbon, π electrons are localized in the respective regions of the two biphenyl derivatives. For example, the compounds denoted by chemical formulas (2) and (5) correspond to this structure.

In a structure in which [A] is a double bond of carbon and the two biphenyl derivatives are bonded in a conjugated system, π electrons spread over the entire molecule, allowing the compound to demonstrate excellent fluorescence. For example, a benzochrysene derivative (dibenzo[g,p]chrysene) denoted by chemical formula (3) corresponds to this structure.

It is possible to further add a biphenyl derivative at [A] to form a three-dimensional propeller structure. Such a structure provides an organic compound which is unlikely to crystallize and has a high glass transition temperature Tg. A compound expressed by chemical formula (4), for example, corresponds to this structure.

Substituents $R_1$, $R_2$, $R_3$, and $R_4$

The compound can be imparted with an electronic characteristic in accordance with its usage by altering the substituents $R_1$, $R_2$, $R_3$, and $R_4$. For example, by introducing diphenylamino group ($NPh_2$—) for all of $R_1$–$R_4$, enhanced hole transport property can be achieved. Some compounds may demonstrate emissive property in addition to hole transport property. By introducing groups such as oxadiazole groups and triazole groups for $R_1$–$R_4$, for example, electron transport property can be demonstrated. Further, by introducing one of diphenylamino group and oxadiazole group in the positions of $R_1$ and $R_2$, while introducing the other of diphenylamino group and oxadiazole group in the positions of $R_3$ and $R_4$, a compound having both the hole transport and electron transport properties (a bipolar compound) can be accomplished.

When large (bulky) substituents are adopted as the substituents $R_1$–$R_4$, those substituents interfere one another, generating steric hindrance. The compound is thereby imparted with a twisted steric structure. Such a twisted structure can suppress crystallization of the organic compound, achieving a compound having a high glass transition temperature Tg and melting point Tm. By using this compound to create organic EL elements, heat resistance of the elements can be enhanced. Steric hindrance may be generated not only by the above substituents $R_1$–$R_4$, but also by the adjacent $R_9$ and $R_{11}$, and $R_{10}$ and $R_{12}$.

[Embodiment 1]

The organic compound of Embodiment 1 used for the organic compound layer 20 in an organic EL element of the present invention will next be explained.

The organic compound of Embodiment 1 is, as shown in the following chemical formula (2),

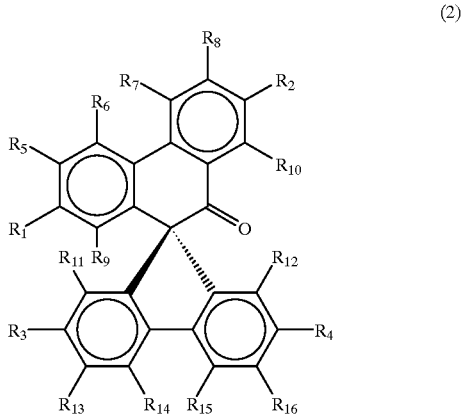

(2)

an asymmetrical spiro compound. One of the skeletons constituting the spiro compound is a fluorene skeleton, while the other structure comprises a skeleton other than fluorene skeleton, thus generating asymmetry in the basic skeleton. In $R_1$–$R_4$ of the above chemical formula (2), substituents of the same type may be used, or substituents of different types may be selected and bonded. Depending on the adopted substituents, the compound can be made to possess an appropriate function such as hole transport property, emissive property, electron transport property, or a combination of those properties. Due to the non-planar molecular structure, a material having high glass transition temperature Tg and excellent heat resistance is provided.

For example, by adopting the structure including oxadiazole groups (shown in row 21 in Table 1 described below), the asymmetrical spiro compound can be used as an electron transport material. When all of $R_1$–$R_4$ are diphenylamino groups ($Ph_2N$ groups) (row 3 of Table 1), the compound is an emissive material having hole transport function, as described later. When all of $R_1$–$R_4$ are diphenylvinyl groups (row 18 of Table 1), the compound can be used as an emissive material. As is readily apparent, the compound can also be employed as an emissive material having electron transport function or an emissive material having hole transport function by adding desired substituents.

The types of substituents applicable as $R_1$–$R_4$ of chemical formula (2) may be selected from, for example, hydrogen, alkyl group, phenyl group, substituted phenyl group, diphenylamino group, diarylamino group, and other groups such as heterocyclic group and substituted heterocyclic group. Electronic and optical properties of the material can be controlled by appropriately selecting substituted phenyl group, condensed polycyclic aromatic ring group, or substituted heterocyclic group. Further, alkyl group, alkoxy group, amino group, nitro group, cyano group, carbonyl group, sulfonyl group, or hydroxyl group may be linked to the phenyl group or the heterocyclic group.

Table 1 below shows examples of possible combinations for $R_1$–$R_4$ using groups such as hydrogen group, t-Bu group, diphenylamino group, oxadiazole group, and other heterocyclic groups.

TABLE 1
| No. | R1 | R2 |
|---|---|---|
| 1 | H | H |
| 2 | t-Bu | t-Bu |
| 3 | 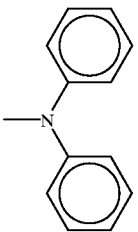 | 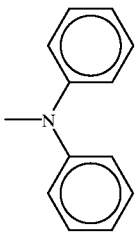 |
| 4 | 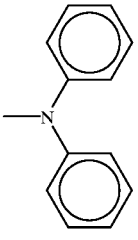 | 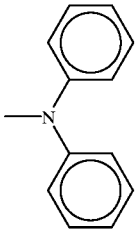 |
| 5 | 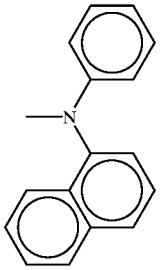 | 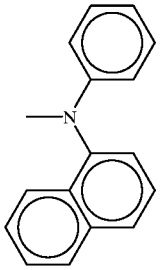 |
| 6 | 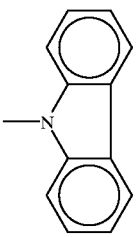 | 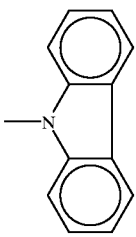 |
| 7 | H | H |
| 8 | 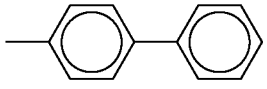 | 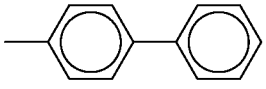 |
| 9 | H | H |
| 10 | t-Bu | t-Bu |
| 11 | 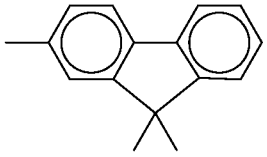 | 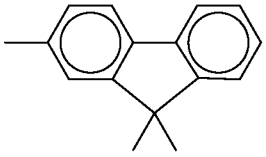 |
| 12 | H | H |
| 13 | t-Bu | t-Bu |

TABLE 1-continued
| | | |
|---|---|---|
| 14 | 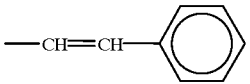 | 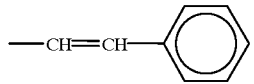 |
| 15 | H | H |
| 16 | t-Bu | t-Bu |
| 17 | 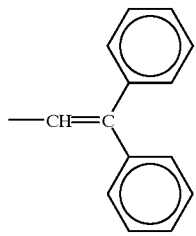 | 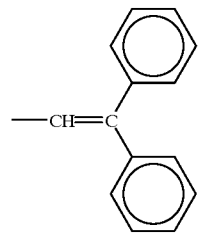 |
| 18 | 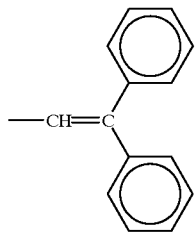 | 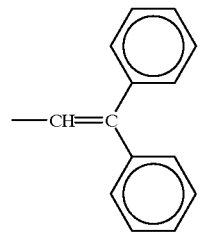 |
| 19 | H | H |
| 20 | t-Bu | t-Bu |
| 21 | 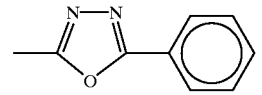 | 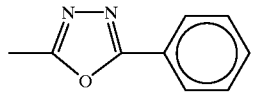 |
| 22 | 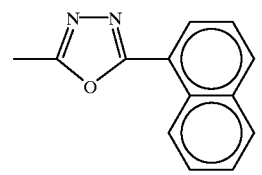 | 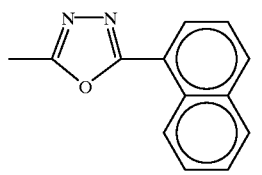 |
| 23 | 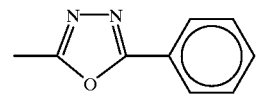 | 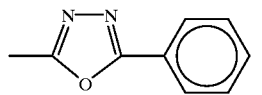 |
| 24 | 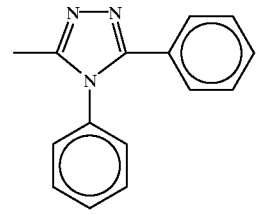 | 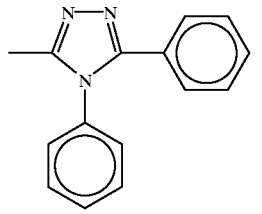 |
| 25 | 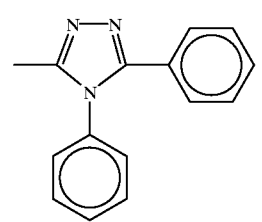 | 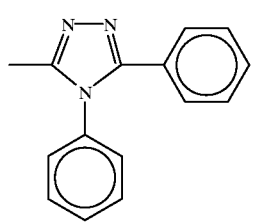 |

TABLE 1-continued
| | | |
|---|---|---|
| 26 | 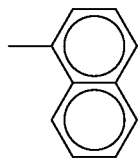 | 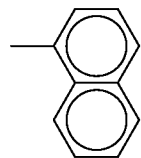 |
| 27 | 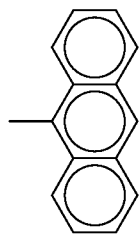 | 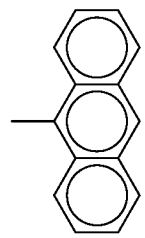 |
| 28 | 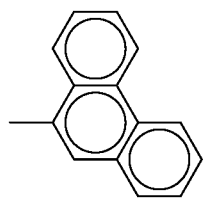 | 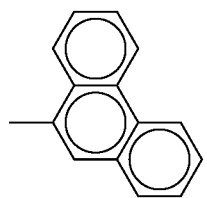 |
| 29 | 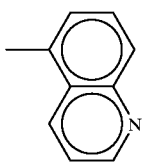 | 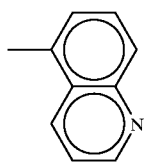 |
| No. | R3 | R4 |
|---|---|---|
| 1 | 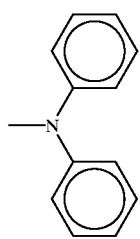 | 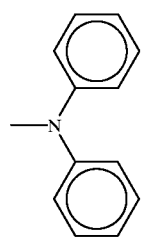 |
| 2 | 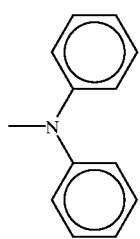 | 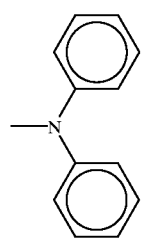 |

TABLE 1-continued
| | | |
|---|---|---|
| 3 | 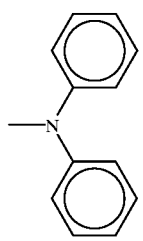 | 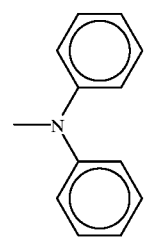 |
| 4 | 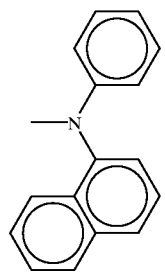 | 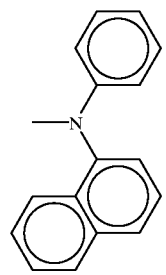 |
| 5 | 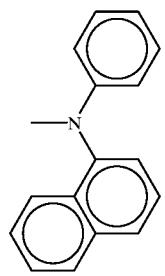 | 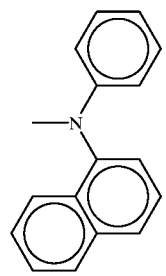 |
| 6 | 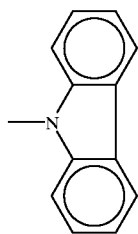 | 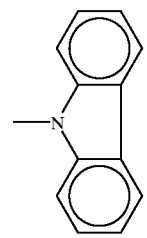 |
| 7 | 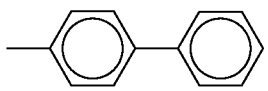 | 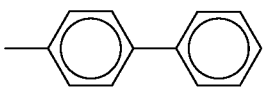 |
| 8 | 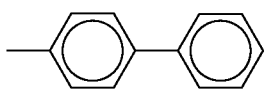 | 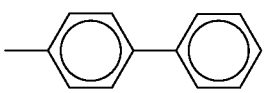 |
| 9 | 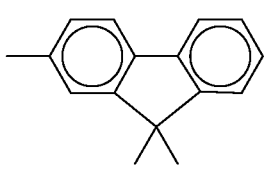 | 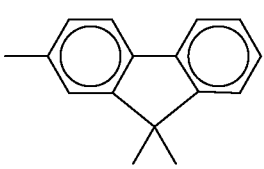 |

TABLE 1-continued
10 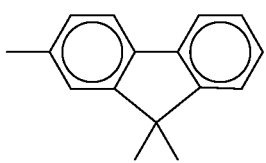 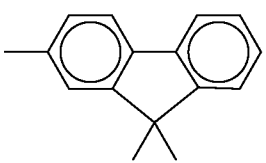
11 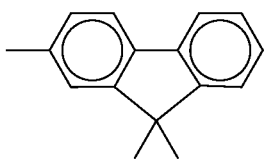 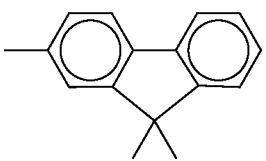
12 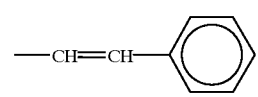 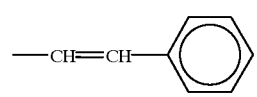
13 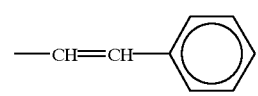 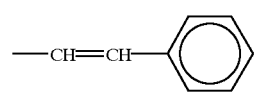
14 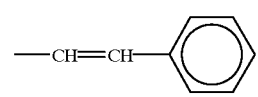 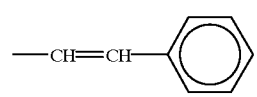
15 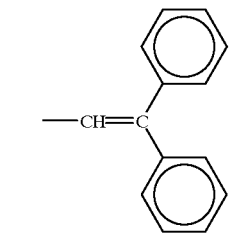 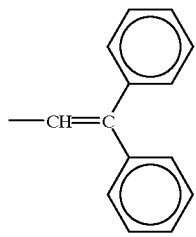
16 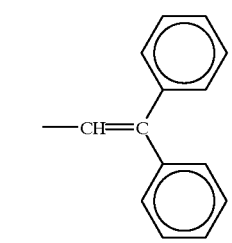 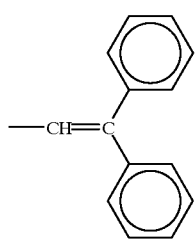
17 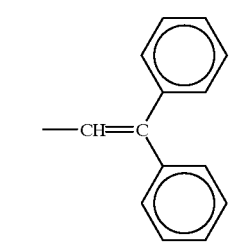 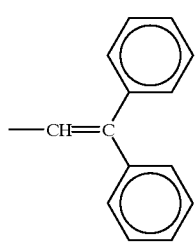

TABLE 1-continued
| | | |
|---|---|---|
| 18 | 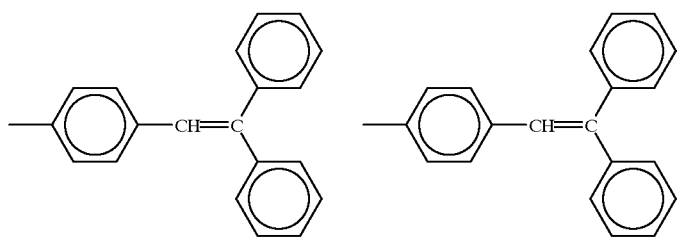 | |
| 19 |  | |
| 20 |  | |
| 21 |  | |
| 22 | 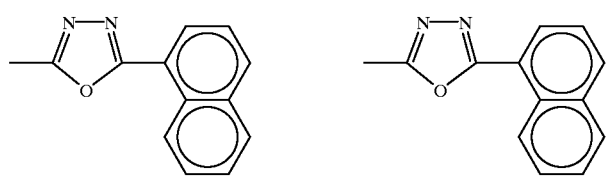 | |
| 23 | 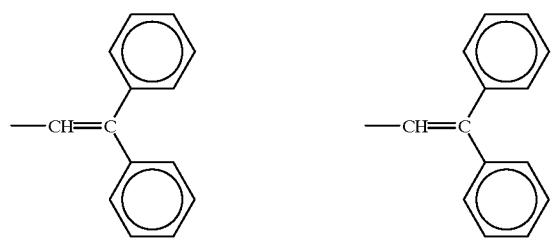 | |
| 24 | 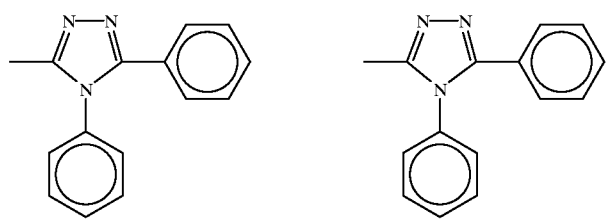 | |
| 25 | 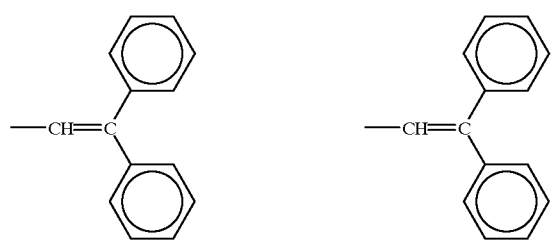 | |

TABLE 1-continued

| | | |
|---|---|---|
| 26 | 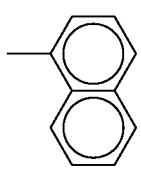 | 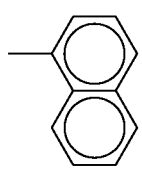 |
| 27 | 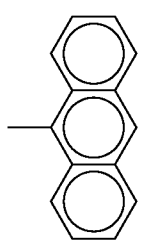 | 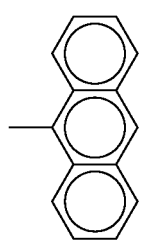 |
| 28 | 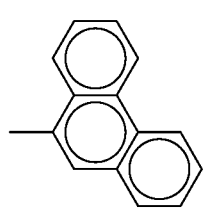 | 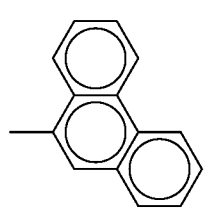 |
| 29 | 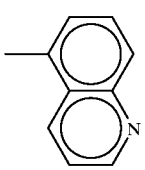 | 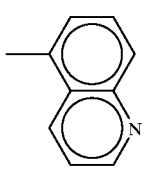 |

By altering the substituents as above, various structures and characteristics can be achieved. Using the compound of the resent invention, performance of the organic compound layer can e enhanced, and higher heat resistance and longer life can be accomplished. Furthermore, the organic compound layer can be easily formed at a reduced thickness.

Moreover, as the molecular structure of the organic compound given bychemical formula (2) is introduced with branches and non-planarity intermolecular aggregation strength is reduced, suppressing crystallizing property. The compound can therefore serve as a stable material having a high glass transition temperature and high heat resistance, which can improve the life of the organic EL elements. Further, the compound includes groups having relatively strong polarity (carbonyl groups) within the basic skeleton. The presence of these groups enhances the adhesion property of the organic material layer to the element electrode, allowing further improvement of element life.

[Embodiment 2]

The organic compound of Embodiment 2 used for the organic compound layer 20 in an organic EL element of present invention will next be explained.

The organic compound of Embodiment 2 has a chemical structure comprising orthotetraphenylene skeleton as the basic skeleton, as denoted by chemical formula (5).

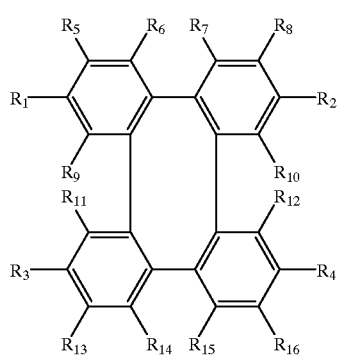

(5)

In this compound having orthotetraphenylene skeleton, the substituent pairs $R_6$ and $R_7$, $R_{10}$, and $R_{12}$, $R_{14}$ and $R_{15}$, and $R_9$ and $R_{11}$, cannot be located within the same plane due to steric hindrance. The compound therefore has a twisted non-planar structure. The non-planar structure allows the compound to have reduced intermolecular aggregation strength, decreased crystallization property, a glass transition temperature Tg above 100° C. excellent heat resistance, and stability. Accordingly, by using this organic compound either alone or in combination with other organic compound materials as the material for the organic compound layer 20, the stability of organic compound layer 20 can be improved.

Further, groups having desired properties can be introduced especially as substituents $R_1$, $R_2$, $R_3$, and $R_4$ among the plurality of substituents R₁–R₁₆, to allow the compound having orthotetraphenylene skeleton to possess hole transport property, emissive property, or electron transport property. Accordingly, the orthotetraphenylene skeleton compound can easily be used as various organic materials for organic EL elements.

While example combinations shown in the above Table 1 can be applied to the substituents $R_1$, $R_2$, $R_3$, and $R_4$, each of the substituents may be selected from hydrogen, alkyl group, alkoxy group, phenyl group, substituted phenyl group, diphenylamino group, diarylamino group, and other groups such as heterocyclic group and substituted heterocyclic group. The selection of other substituents ($R_5$–$R_{16}$) in chemical formula (5) is not restricted.

For example, as shown in rows 1–6 in Table 1, by using a diphenylamino group (Ph₂N group) or its partially substituted body for any or all of $R_1$, $R_2$, $R_3$, and $R_4$, the compound can be made to serve as a hole transport material.

Furthermore, as shown in rows 15–18 in Table 1, when using a diphenylvinylene group for any or all of $R_1$–$R_4$, the compound can serve as a blue emissive material.

The compound can be used as an emissive material also when a biphenyl group is used for any or all of $R_1$–$R_4$ as shown in rows 7 and 8 in Table 1, when a fluorenyl group is used for any or all of $R_1$–$R_4$ as shown in rows 9–11 in Table 1, and when a styryl group is used for any or all of $R_1$–$R_4$ as shown in rows 12–14 in Table 1.

Moreover, when using a phenyloxadiazole group or its derivative for any or all of $R_1$–$R_4$ as shown in rows 19–22 in Table 1, the compound can function as an electron transport material or an emissive material having electron transport property.

By altering the substituents as described above, various structures and characteristics can be achieved. Using the organic compound according to Embodiment 2 to form organic EL elements, performance of the organic compound layer can be enhanced, and higher heat resistance and longer life can be accomplished. Furthermore, such an organic compound layer can be easily formed at a reduced thickness because the compound is unlikely to crystallize and maintains amorphousness.

[Embodiment 3]

The organic compound of Embodiment 3 for use in the organic compound layer 20 of an organic EL element has a chemical structure wherein two biphenyl derivatives are linked via a double bond, as denoted by chemical formula (3).

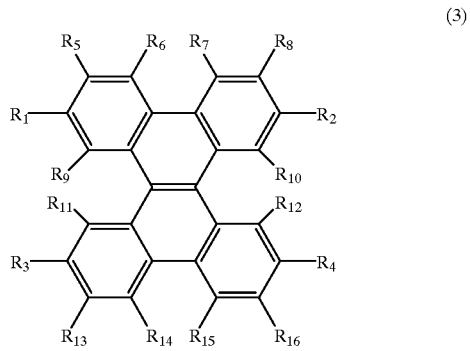

(3)

In this organic compound, similar to the orthotetraphenylene skeleton compound of the above Embodiment 2, the substituents $R_6$ and $R_7$, $R_{10}$ and $R_{12}$, $R_{14}$ and $R_{15}$, and $R_9$ and $R_{11}$ are relatively closely positioned, and, due to steric hindrance, are unlikely to be located within the same plane. The compound therefore tends to have a twisted non-planar structure, which allows the compound to be a stable material having a high glass transition temperature Tg. Because the structure of the compound has a remarkably developed conjugated system, it can be expected to demonstrate emissive property based on only this aspect. In a similar manner as the above Embodiments 1 and 2, use of this organic compound either alone or in combination with other organic compound materials as the material for the organic compound layer 20 contributes to enhanced stability and high performance of organic compound layer 20.

Further, groups having desired properties can be introduced especially as substituents $R_1$, $R_2$, $R_3$, and $R_4$ among the plurality of substituents $R_1$–$R_{16}$, to impart the compound with hole transport property, emissive property, electron transport property, or a plurality of those properties. The compound can therefore be easily used as various organic materials for organic EL elements.

While example combinations shown in the above Table 1 can be applied to the substituents $R_{10}$, $R_2$ $R_3$, and $R_4$ as in the above Embodiments 1 and 2, each of the substituents may be selected from hydrogen, alkyl group, alkoxy group, phenyl group, substituted phenyl group, diphenylamino group, diarylamino group, and other groups such as heterocyclic group and substituted heterocyclic group. The selection of the other substituents ($R_5$–$R_{16}$) in chemical formula (3) is not restricted.

For example, as shown in rows 1–6 in Table 1, by using a diphenylamino group (Ph₂N group) or its partially substituted body for any or all of $R_1$, $R_2$, $R_3$, and $R_4$, an emissive material that simultaneously serve the hole transport function can be obtained.

As in Embodiment 2, when using a diphenylvinylene group for any or all of $R_1$–$R_4$ as shown in rows 15–18 in Table 1, the compound can serve as an emissive material.

As in Embodiment 2, the compound can also serve as an emissive material when a biphenyl group is used for any or all of $R_1$–$R_4$ as shown in rows 7 and 8 in Table 1, when a fluorenyl group is used for any or all of $R_1$–$R_4$ as shown in rows 9–11 in Table 1, or when a styryl group is used for any or all of $R_1$–$R_4$ as shown in rows 12–14 in Table 1.

Moreover, when using a phenyloxadiazole group for any or all of $R_1$–$R_4$ as shown in rows 19–23 in Table 1, the compound can function as an emissive material having electron transport property, similarly to Embodiment 2.

By altering the substituents as described above, various structures and characteristics can be achieved. Using the organic compound according to Embodiment 3, performance of the organic compound layer can be enhanced, and higher heat resistance and longer life can be accomplished. Furthermore, such an organic compound layer can easily be formed at a reduced thickness.

[Embodiment 4]

The organic compound of Embodiment 4 used for the organic compound layer 20 in an organic EL element of the present invention will next be explained. The organic compound of Embodiment 4 has a chemical structure denoted by chemical formula (4),

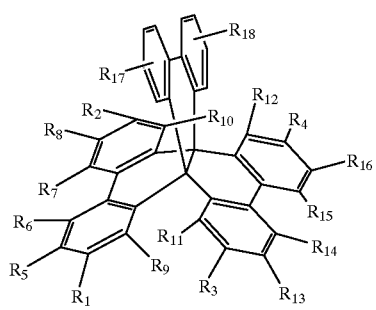

(4)

wherein three biphenyl derivatives are linked via a single carbon bond.

Because the compound of chemical formula (4) has a three-dimensional propeller structure as shown, the glass transition temperature Tg is very high. It is therefore possible to obtain a stable organic compound layer that is unlikely to crystallize even when formed into a thin film.

Further, groups having desired properties can be introduced especially as substituents $R_1$–$R_4$ among the plurality of substituents $R_1$–$R_{16}$, $R_{17}$, and $R_{18}$, to impart the compound with properties such as emissive property, hole transport property, and electron transport property. It is further possible to allow a single organic compound to possess a plurality of functions such as the hole transport property and emissive property, the electron transport property and emissive property, or all of those properties.

While example combinations shown in the above Table 1 can be applied to the substituents $R_1$, $R_2$, $R_3$, and $R_4$ as in the above Embodiments 1–3, each of the substituents may be selected from hydrogen, alkyl group, alkoxy group, phenyl group, substituted phenyl group, diphenylamino group, diarylamino group, and other groups such as heterocyclic group and substituted heterocyclic group. No particular restrictions exist for other substituents ($R_5$–$R_{18}$) in chemical formula (4).

For example, as shown in rows 1–6 in Table 1, by using a diphenylamino group ($Ph_2N$ group) or its partially substituted body for any or all of $R_1$, $R_2$, $R_3$, and $R_4$, hole transport function can be achieved.

EXAMPLES

Example 1

Example 1 related to the above Embodiment 1 will now be explained. In Example 1, as an orthotetraphenylene derivative denoted by chemical formula (2), a compound expressed by chemical formula (6)

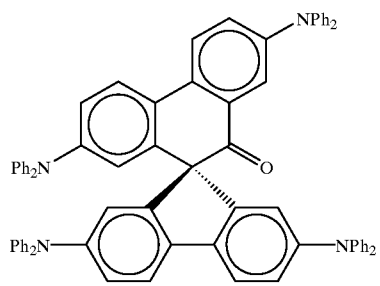

(6)

was produced, and used as an emissive material having hole transport function in an emissive layer of an organic EL element.

Synthesis Example 1

The synthesis method for the compound of chemical formula (6), which is one type of the compound denoted by chemical formula (2), is described while referring to the following chemical reaction formula (7). The compound of chemical formula (6) is identical with the compound C shown in the chemical reaction formula (7). Further, this compound is the compound obtained when adopting diphenylamino groups for $R_1$–$R_4$ in the general compound formula (2).

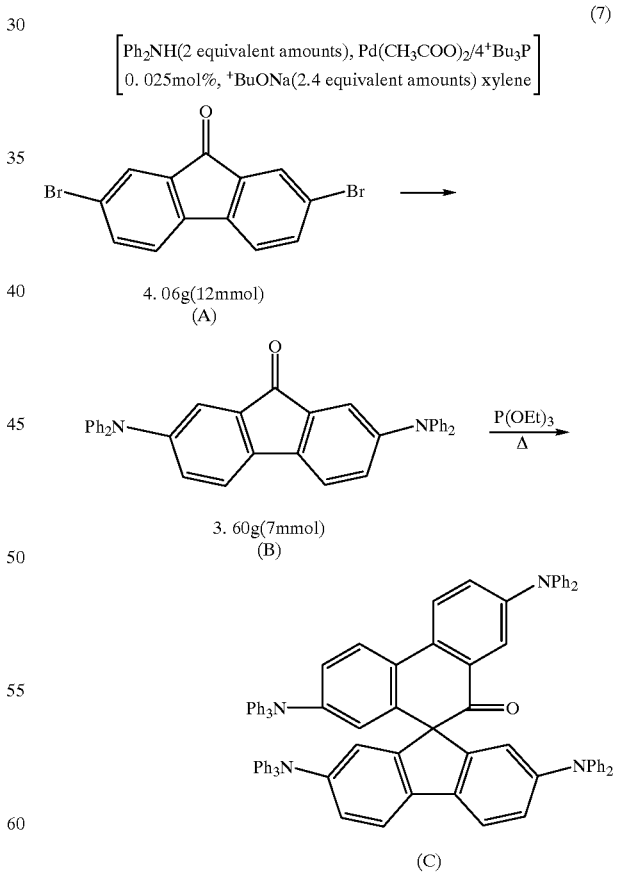

(7)

(From Compound A to Compound B)

A catalyst solution was prepared in advance by mixing palladium acetate and tri-t-butylphosphine (at the molar ratio of 1:4) in xylene.

2,7-dibromo-9-fluorene (4.06 g: 12 mmol) shown as compound A, 2 equivalent amounts of 1-naphthylphenylamine (a secondary amine), and a xylene mixture of 2.4 equivalent amounts of sodium t-butoxide were, after adding the above catalyst solution for an amount equivalent to 1 mol %, maintained at 120° C. for 3 hours in a nitrogen atmosphere. After benzene extraction, standard processing was performed, and the product was purified by column chromatography to obtain 2,7-bis(diphenylamino)-9-fluorenone indicated as compound B. The melting point of the resulting compound B was 217° C.–218° C.

(From Compound B to Compound C)

3.60 g (7 mmol) of 2,7-bis(diphenylamino)-9-fluorenone indicated as compound B was mixed with 15 g triethyl phosphite [P(OEt)$_3$)], and heated in nitrogen atmosphere to 140° C. for 24 hours. The raw materials were almost completely eliminated by this procedure. The reacted mixture was concentrated under reduced pressure, then separated and dried using benzene or chloroform. The obtained raw product was purified by column chromatography to provide 3.8 g (yield 75%) of compound C denoted by chemical formula (6). The melting point of the resulting compound C was 300° C. or higher. Its glass transition temperature was observed to be approximately 140° C.

Element Production Example 1

An organic EL element produced using the compound of chemical formula (6) obtained by the above Synthesis Example 1 has a configuration as shown in FIG. 1(c). Referring now to FIG. 2 (although the specific structure of the organic compound layer 20 differs from that of FIG. 2), the element comprised a glass substrate (transparent substrate) 10 having ITO disposed at a film thickness of 1800 Å. On this substrate an emissive layer of 600 Å was formed using the asymmetrical spiro compound of the above chemical formula (6) as the emissive material that also functions as a hole transport layer. Over the emissive layer, Alq$_3$ expressed by the following chemical formula

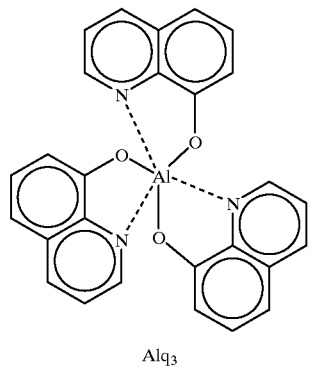

Alq$_3$ was disposed at a thickness of 600 Å as the electron transport layer. Subsequently, a lamination of LiF at 5 Å and Al at 1600 Å was formed as the metal cathode 18. The organic compound layer 20 and the metal cathode 18 were sequentially formed by vacuum deposition. The degree of vacuum during the deposition procedure was 6×10$^{-7}$ Torr.

Figure 3:
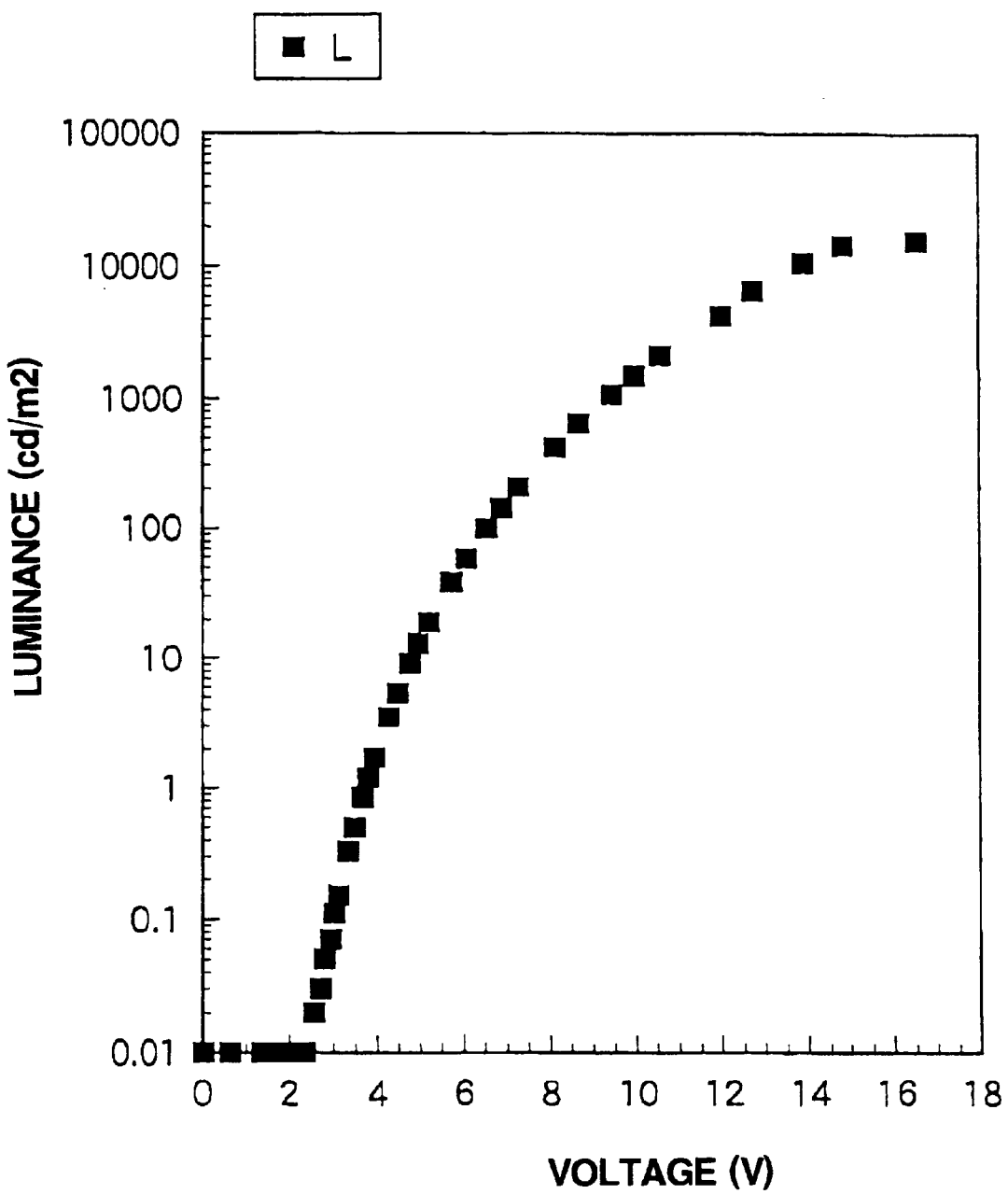
FIG. 3 is a diagram illustrating the relationship between the applied voltage and the emission luminance in an organic EL element using the organic compound (6) according to Example 1 of the present invention.
Figure 4:
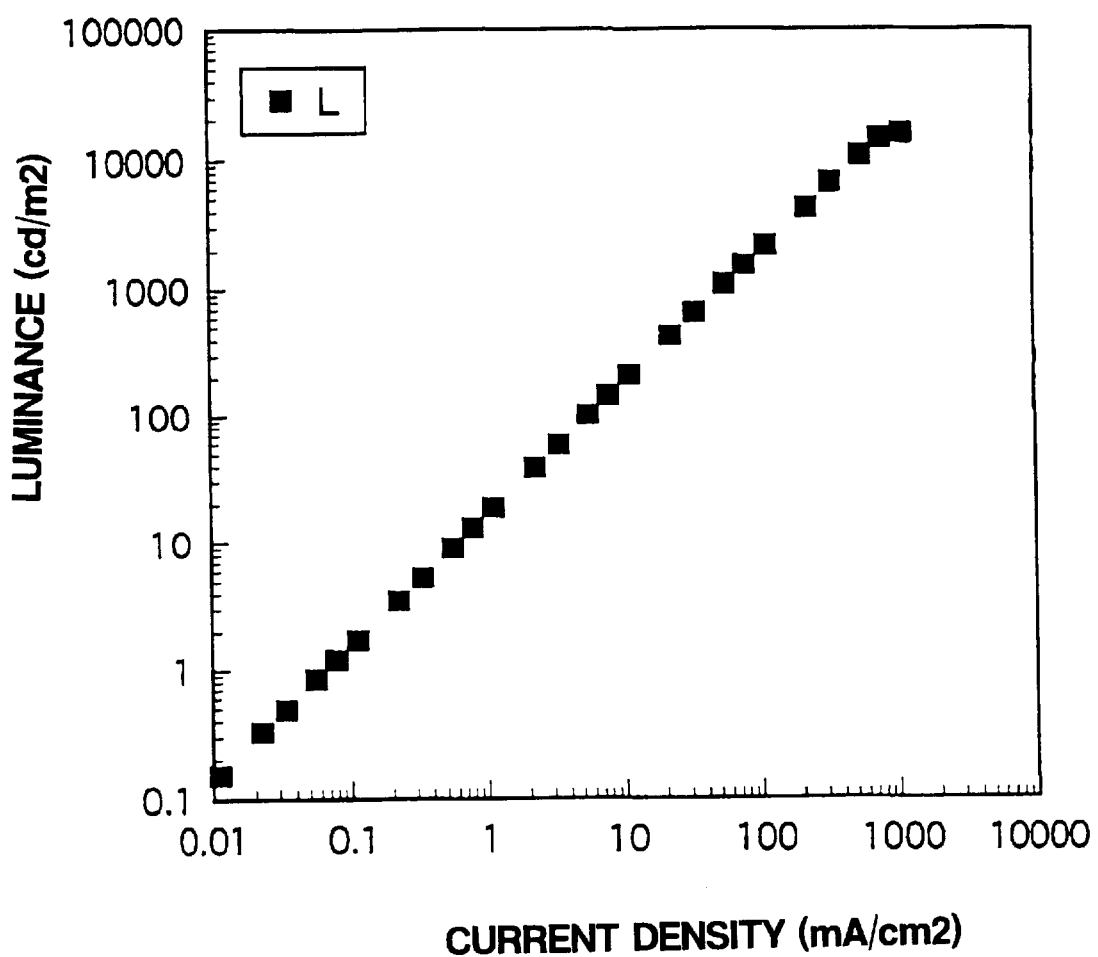
FIG. 4 is a diagram illustrating the relationship between the density of the supplied current and the emission luminance in an organic EL element using the organic compound (6) according to Example 1 of the present invention.

When a positive voltage was applied on the ITO side and a negative voltage on the metal side of the organic EL element created as described above, results as shown in FIG. 3 were obtained. In FIG. 3, the vertical axis indicates luminance (cd/m$^2$), while the horizontal axis indicates the applied voltage (V). As can be seen in FIG. 3, it was confirmed that the created element demonstrated stable light emission from very low applied voltage (2.2V, for example). When a direct current of 6V was applied, a yellow light emission (emission wavelength peak: 545 nm) generated from the compound of chemical formula (6) was obtained at the luminance of approximately 100 cd/m$^2$. Further, as shown in FIG. 4, the emission luminance (vertical axis) increased at a constant ratio with respect to the current density supplied to the element (horizontal axis), confirming that the element has a stable emission characteristic. Moreover, in examining the change of emission luminance over operation time, it was found that the element of the present Example 1 can achieve a half decay lifetime of approximately 5000 hours in a continuous operation at 300 cd/m$^2$. For the emission efficiency, 3.5 lm/W was achieved.

It is believed that the prolonged life of the element could be achieved as described above because the compound denoted by chemical formula (6) adheves well to ITO, and has a high glass transition temperature. The preferable adhesion property of the compound denoted by chemical formula (6) to ITO may result from the adhesion property displayed with respect to ITO by, for example, a carbonyl group of the cyclohexanon within the structure pairing with the fluorene skeleton in the molecular structure of the compound.

Comparison Example 1

On a glass substrate having ITO disposed at a film thickness of 1800 Å, a hole transport layer composed of a diamine derivative (α-NPD) expressed by the following chemical formula (8)

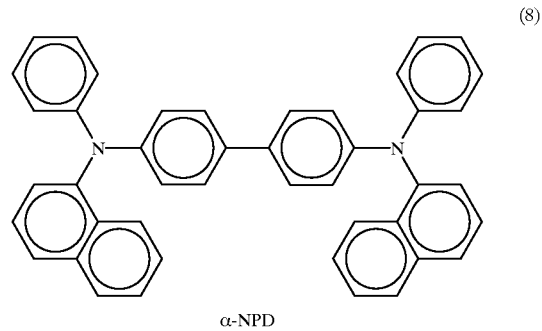

α-NPD was formed at a thickness of 600 Å. Alq$_3$ was then deposited at 600 Å as an emissive layer. As a cathode, a lamination of LiF at 5 Å and Al at 1600 Å was formed. The organic compound layer and the cathode were sequentially formed by vacuum deposition. The degree of vacuum during the deposition procedure was 6×10$^{-7}$ Torr.

When a positive voltage was applied on the ITO side and a negative voltage on the metal side of the organic EL element created as described above, the element operation was unstable at low voltages. When a direct current of 6V was applied, a green light emission (emission wavelength peak 530 nm) generated from Alq$_3$ was obtained only at approximately 50 cd/M$^2$. The half decay lifetime of this element was approximately 3000 hours of continuous operation at 300 cd/M$^2$.

As is apparent from the comparison between the above Example 1 and the Comparison Example 1, it is observed that, by creating an organic EL element using the organic compound according to Embodiment 1 of the present invention, a stable element having high luminance can be accomplished.

Example 2-1

Example 2-1 related to the above Embodiment 2 will next be explained. In Example 2-1, as an orthotetraphenylene derivative denoted by chemical formula (5), the compound having diphenylamino groups (NPh$_2$—) introduced as the substituents R$_1$–R$_4$ as denoted by chemical formula (9)

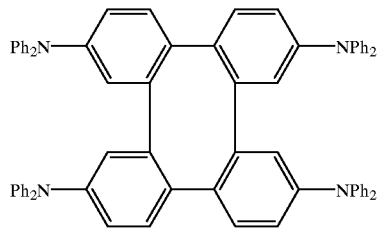

(9)

was synthesized, and used as a material for the hole transport layer of an organic EL element.

Synthesis Example 2-1

The synthesis method for the compound of chemical formula (9) will be described while referring to the following chemical reaction formula (10).

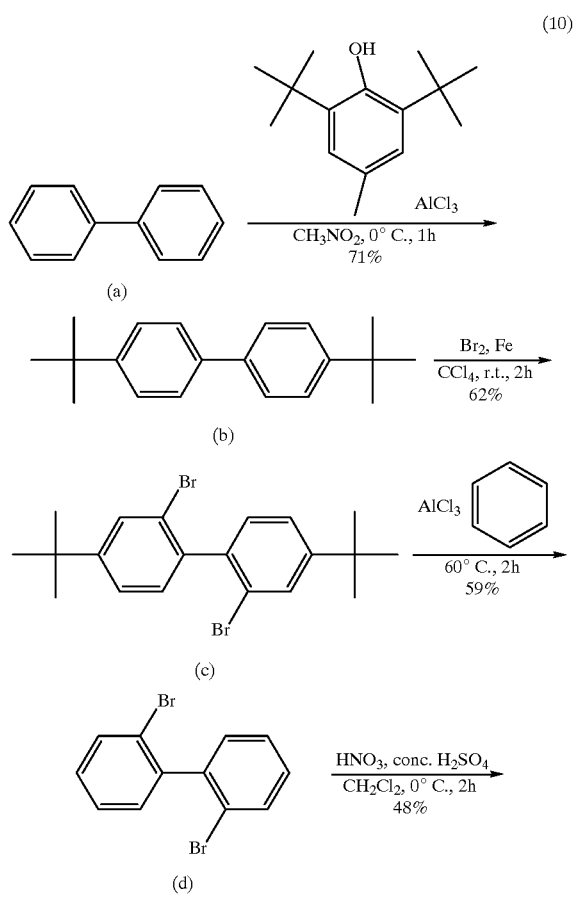

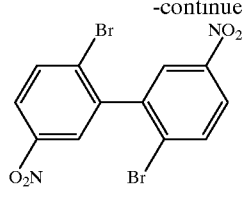

(e)

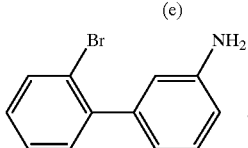

(f)

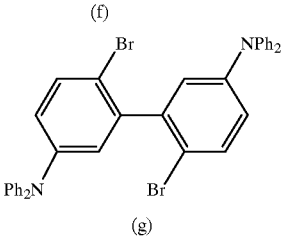

(g)

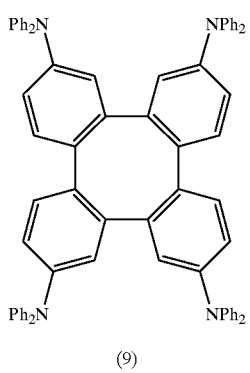

(9)

(i) Synthesis Process from Biphenyl (Chemical Formula (a)) to 2,2'-dibromo-5,5'-dinitrobiphenyl (Chemical Formula (e))

In accordance with the method disclosed in T. K. Drugherty, K. S. Y. Lau, J. Org. Chem., 48, 5273 (1983), biphenyl denoted by chemical formula (a) was used as the starting material, and →4,4'-di(t-butyl)biphenyl (chemical formula (b))
→2,2'-dibromo-4,4'-di(t-butyl)biphenyl (chemical formula (c))
→2,2'-dibromobiphenyl (chemical formula (d))
→2,2'-dibromo-5,5'-dinitrobiphenyl (chemical formula (e))
were synthesized.

(ii) Synthesis of 5,5'-diamino-2,2'-dibromobiphenyl (Chemical Formula (f))

2.01 g (5.0 mmol) of the compound of chemical formula (e) obtained by the above (i) was placed in a 100 ml three-neck flask. 23 ml THF (tetrahydrofuran) and 18 ml EtOH (ethanol) were added. After stirring, 30 ml concentrated hydrochloric acid was added. Subsequently, a total of 4.47 g (80 mmol) Fe was added at two separate times. After H$_2$ generation has somewhat waned, the reaction system was refluxed and left over one night. After cooling, the product was examined by high performance liquid chromatography (HPLC). The solution of the reaction system was poured into a 300 ml conical beaker containing a large amount of ice. The raw materials were eliminated by extraction using 200 ml PhH (benzene). The aqueous layer was displaced to a different separating funnel, and extraction was performed by adding 200 ml PhH and 200 ml 2N NaOH. Through this process, the product given by chemical formula (f) was transferred to the organic layer. Further, the product was rinsed with water, rinsed with brine, and dried using $MgSO_4$. After eliminating the solvent, the product was recrystallized using EtOH, filtered, and vacuum dried. The obtained brownish crystal was identified as a single crystal by FAB-MS and $^1$HNMR. The yield amount was 1.10 g (3.2 mmol), and the yield rate was 65%. HPLC: retention time=3.32 min. FAB-MS: m/z 342(M+2). $^1$HNMR ($CDCl_3$, TMS) δ=7.37 (dd, 2H, J=8.2, 2.8 Hz), 6.58 (dd, 2H, J=8.2, 2.8 Hz), 6.56 (S, 2H), 3.72 (br.s, 4H). Melting point (m.p.)=127° C.–130° C.

(iii) Synthesis of 2,2'-dibromo-5,5'-di(diphenylamino)biphenyl (Chemical Formula (g))

1.70 g (5.0 mmol) of the obtained compound of chemical formula (f) and 2.71 g (28 mmol) t-BuONa were placed in a 30 ml three-neck flask, and subjected to vacuum degassing and $N_2$ substitution. 10 ml (90 mmol) PhI and 1 ml o-xylene were poured in, and the reaction system was stirred and kept at 50° C. Subsequently, 2.0 ml (1.9 μmol) Pd regulator solution (α) was poured in. This reaction system was maintained at 110° C. and left overnight. In the meantime, white solid matter precipitated, which is considered to be NaI. After cooling, the product was confirmed by HPLC. The solution of the reaction system was then poured into a 300 ml conical beaker containing ice and $CHCl_3$. 8 ml 1N HCl was added to make the solution acidic. The product was extracted using $CHCl_3$, rinsed with water, rinsed with brine, and dried using $MgSO_4$. After eliminating the solvent, PhI was removed by vacuum concentration (90° C./28 mmHg). The remaining solid matter was dissolved into $CHCl_3$, then adsorbed to sellite to eliminate $CHCl_3$. Using this sellite, separation was performed by silica gel column chromatography ($CHCl_3$:hexane=1:3). The obtained crystal was vacuum dried, and then confirmed as a single crystal by FAB-MS and $^1$HNMR. The yield amount was 2.30 g (3.6 mmol), and the yield rate was 72%. HPLC: retention time= 23.8 min. FAB-MS: m/z 646($M^+$+2). $^1$HNMR ($CDCl_3$, TMS) δ=7.41 (d, 2H, J=8.7 Hz), 7.29 (m, 2H), 7.25 (m. 3H), 7.22 (m, 3H), 7.11–7.17 (m, 5H), 7.05–7.10 (m, 5H), 7.01–7.04 (m, 2H), 7.00 (d, 2H, J=2.8 Hz), 6.88 (dd, 2H, J=8.7, 2.8 Hz). Melting point (m.p.)=217° C.–230° C.

(iv) Synthesis of 2,7,10,15-tetrakis(diphenylamino)tetra-o-phenylene (Chemical Formula (5))

Figure 5:
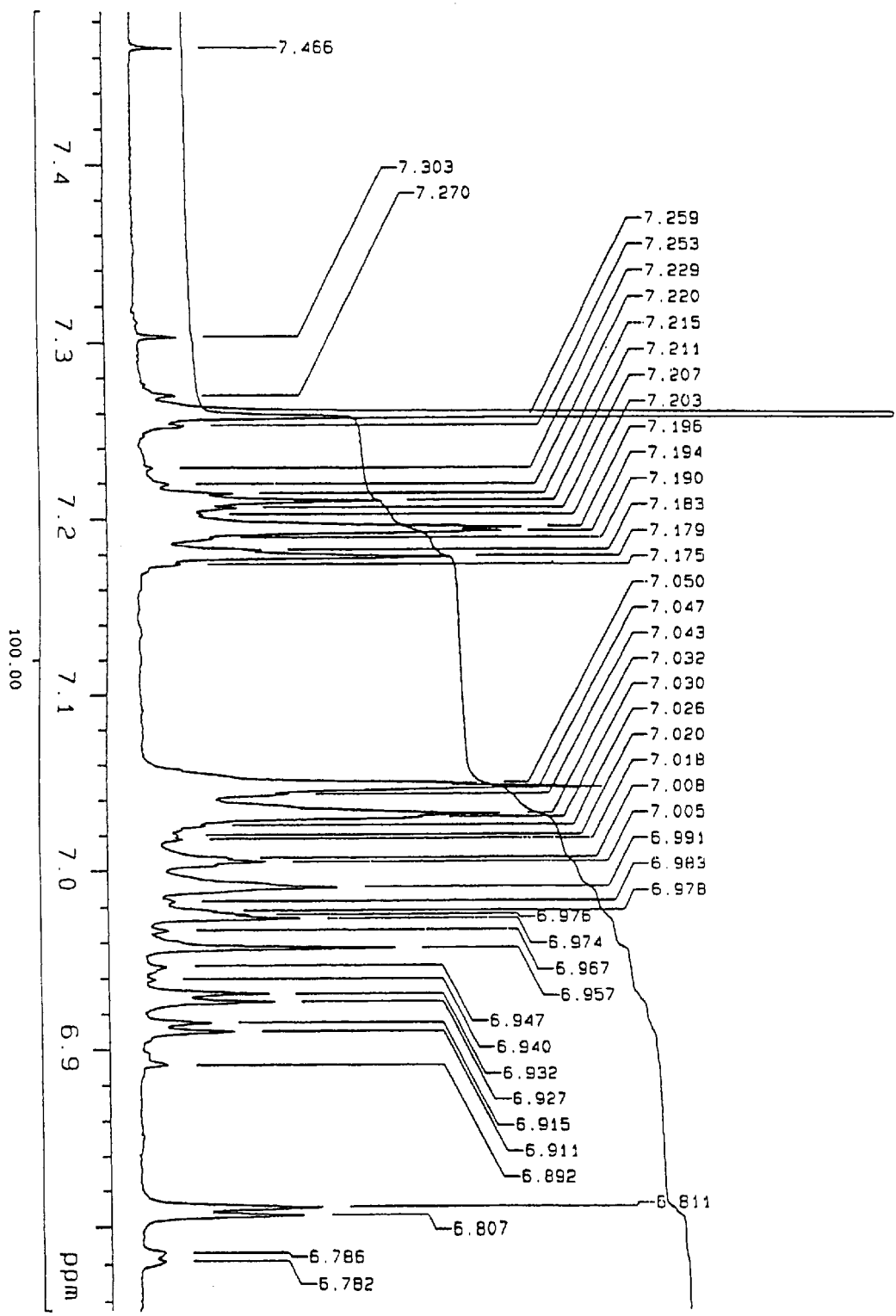
FIG. 5 is a diagram showing the $^1$HNMR spectrum of the organic compound (9) according to Example 2.
Figure 6:
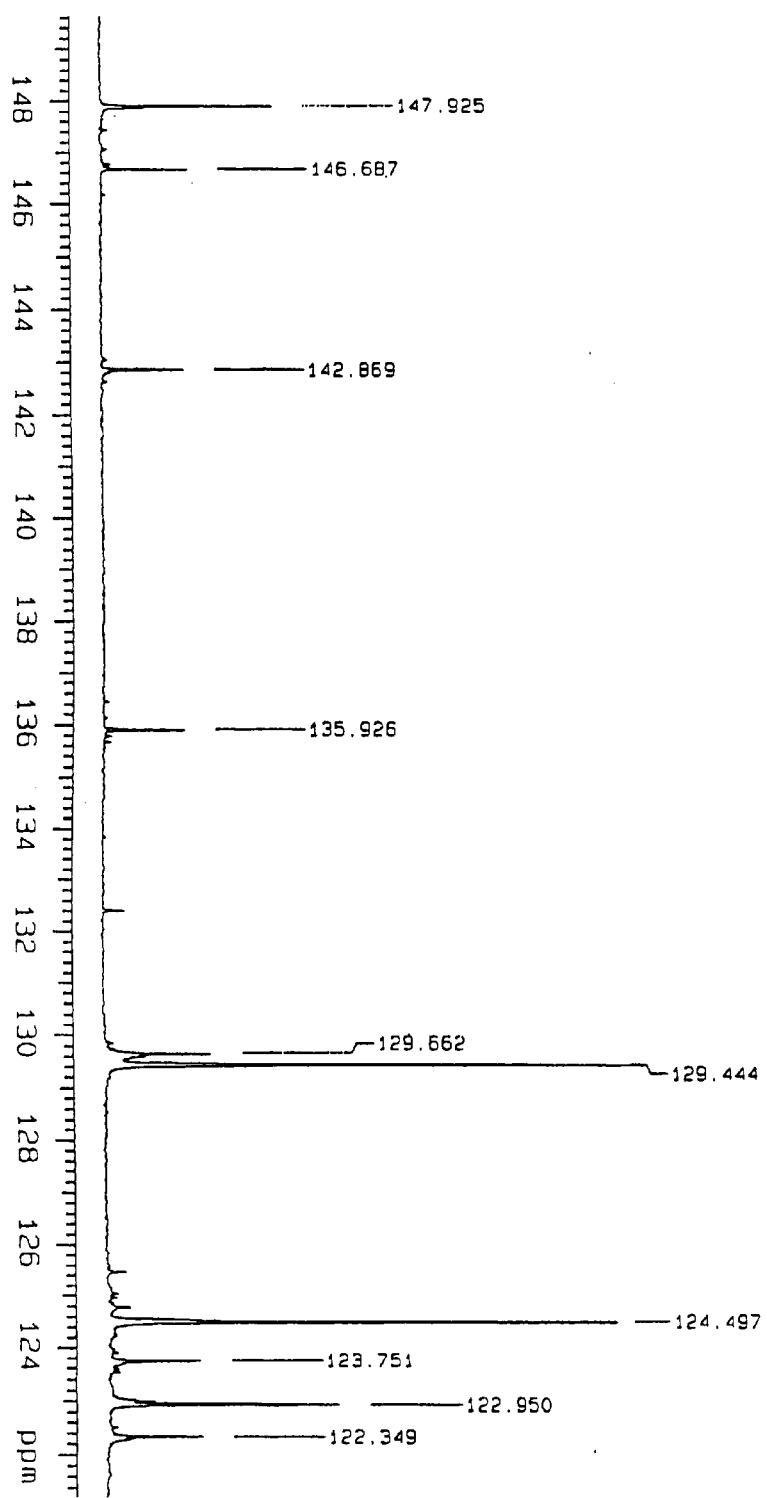
FIG. 6 is a diagram showing the $^{13}$CNMR spectrum of the organic compound (9) according to Example 2.

The compound obtained by the above (iii) and denoted by the chemical formula (g) and anhydrous $CuBr_2$ were vacuum heated and dried. 2.30 g (3.6 mmol) of the obtained compound was then placed in a 50 ml four-neck flask, while 4.02 g (18 mmol) of the anhydrous $CuBr_2$ was placed in a Thunberg tube. After the Thunberg tube was greased and installed on the flask, the reaction system was subjected to vacuum degassing and $N_2$ substitution. 3 ml dry THF and 6 ml toluene were then poured in. The reaction system was stirred and cooled to −78° C. Subsequently, 5.6 ml (10 mmol) hexane solution of n-BuLi was added, and the temperature was raised to 0° C. to promote lithiation. The temperature was again lowered to −78° C. and left for two hours. The Thunberg tube was then turned to add $CuBr_2$ to the compound, and the reaction system was left overnight to allow cyclization to occur. Subsequently, the reaction was quenched by adding 30 ml 1N HCl. The product was extracted using $CHCl_3$ (200 ml), rinsed with 300 ml 1N HCl to remove $CuBr_2$, rinsed with water, rinsed with brine, and dried using $MgSO_4$. After the solvent was eliminated, the remaining solid matter was dissolved into $CHCl_3$, then adsorbed to sellite to eliminate $CHCl_3$. Using this sellite, separation was performed by silica gel column chromatography ($CHCl_3$:hexane=1:1). The mixture containing the product was further separated by GPC (gel permeation chromatography). The obtained crystal was vacuum dried, and then confirmed as a single crystal by HPLC and FAB-MS. The yield amount was 0.168 g, while the yield rate was 35%. HPLC: retention time=120min. FAB-MS: m/z 972 ($m^+$). The measurement results obtained by $^1$HNMR ($CDCl_3$, TMS) were as shown in FIG. 5 (500 MHz). The measurement results by $^{13}$CNMR (500 MHz) were as shown in FIG. 6.

The melting point (m.p.) was 283° C.–287° C. The glass transition temperature Tg of this organic compound was examined to be remarkably high, at 147° C., and it was found that the compound demonstrated a high heat resistance. The examined glass transition temperature is very high, at the same level as the glass transition temperature of alumiquinolinol complex ($Alq_3$) conventionally used widely as an emissive material. By using this organic compound as, for example, the hole transport layer, heat resistance of the organic compound layer can be greatly improved, in light of the fact that the glass transition temperature Tg of TPD, a known hole transport layer material, is approximately 60° C.

Element Production Example 2-1

The organic EL element produced using the orthotetraphenylene derivative of chemical formula (9) obtained by the above Synthesis Example 2 had a configuration as described below. Referring to FIG. 2, the element comprised a glass substrate 10 having an ITO layer disposed on its surface in advance to be used as the transparent electrode. Over the transparent electrode 12, the compound of the above chemical formula (9) was formed into a film having a thickness of 600 Å to serve as the hole transport layer. Over this layer, alumiquinolinol complex ($Alq_3$), which is a green emissive material, was used to form the emissive layer 24 at a thickness of 600 Å. A metal electrode 18 was formed over the emissive layer 24. The metal electrode 18 comprised a laminated structure including an $Li_2O$ layer of 5 Å and an Al layer of 1600 Å, formed in that order. In the organic EL element created in this way, the transparent electrode 12 was used as the anode, and the metal electrode 18 as the cathode.

Comparison Example 2-1

Comparison Example2-1 is explained below. Differing from Example 2-1, triphenyldiamine (TPD) expressed by the following chemical formula (11)

(11)

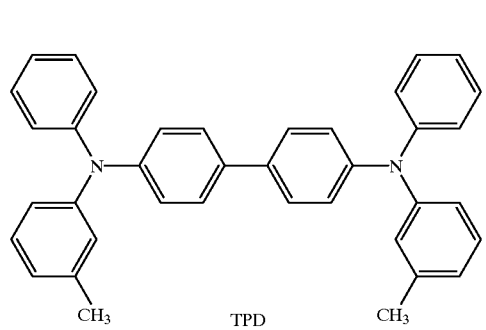

was used as the hole transport layer 22 in Comparison Example 2-1. Other conditions were the same as Example 2-1. Disposed on a glass substrate 10 having ITO were a hole transport layer 22 made of TPD at a thickness of 600 Å, and Alq$_3$ at a thickness of 600 Åas an emissive layer 24. Over the emissive layer 24, a metal electrode 18 was formed by laminating, in order, an Li$_2$O layer of 5 Å and an Al layer of 1600 Å. The organic EL element was thus obtained.

Comparison Results

When a direct current voltage was applied between the transparent electrode 12 and the metal electrode 18 in the organic EL element of Example 2-1, green light emission generated from Alq$_3$ was observed in the emissive layer 24 starting at 3V of the applied voltage. Similarly in the element of Comparison Example 2, green light emission generated from Alq$_3$ was observed in the emissive layer 24 starting at 3V of direct current voltage application.

Figure 7:
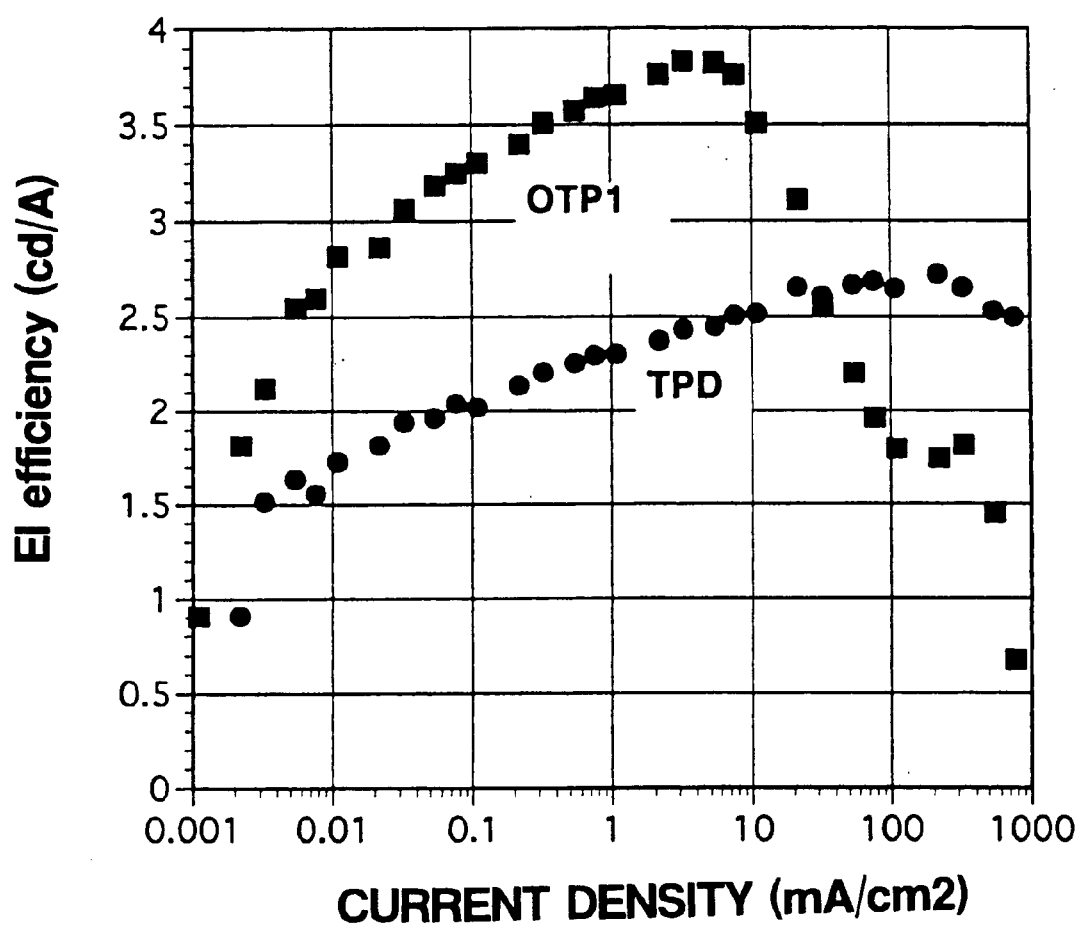
FIG. 7 is a diagram showing the emission luminance in terms of current density of organic EL elements using the organic compound according to Example 2 and the conventionally known TPD.

However, upon examining the emission efficiency characteristics in terms of current density in Example 2-1 and Comparison Example 2-1, it was found, as shown in FIG. 7, that the element of Example 2-1 displayed a very high emission efficiency in the range of low current density. Specifically, the emission efficiency of 4.5 cd/A was accomplished at the luminance of 300 cd/m$^2$. In the element of Comparison Example 2-1, on the other hand, the efficiency for achieving the luminance of 300 cd/m$^2$ was low, at 2.5 cd/A. Example 2 achieved an element life of 1000 hours under the initial condition of 300 cd/m$^2$, while the element life in Comparison Example 2-1 was approximately 800 hours under the same initial condition. It is apparent from these results that, by using the organic compound of Embodiment 2 as the hole transport layer as in Example 2-1, a practical organic EL element with a prolonged element life and enhanced emission efficiency can be obtained.

Example 2-2

Element Production Example 2-2

Similarly in Example 2-2, the orthotetraphenylene derivative expressed by chemical formula (9), which was obtained according to the above Synthesis Example 2-1, was used as the hole transport layer to form an organic EL element. In Element Production Example 2-2 the cathode material differed from that used in the above Element Production Example 2-1. Specifically, the compound of the above chemical formula (9) was used to form the hole transport layer at a thickness of 600 Å. Subsequently, Alq$_3$ was used to form the emissive layer at a thickness of 600 Å. And finally, a metal electrode was formed over the emissive layer. As the metal electrode, MgAg alloy was used to provide a layer of 1800 Å.

Comparison Example 2-2

For comparing with the above Example 2-2, an organic EL element was formed using, as the hole transport layer, α-NPD denoted by the above chemical formula (8), while other conditions were the same as in Production Example 2-2.

Comparison Results

When the elements of Element Production Example 2-2 and Comparison Example 2-2 were operated under the same conditions, green light emission (530 nm) generated from Alq$_3$ was observed in both elements. However, the emission efficiency of the element of Comparison Example 2-2 was only 2.5 cd/A, while the element of Element Production Example 2-2 was high, at 4.5 cd/A. It was thus observed that the emission efficiency can be enhanced by using the organic compound related to the present Example 2-2 as the hole transport layer.

Example 3-1

Example 3-1 related to the above Embodiment 3 will next be explained. In Example 3-1, as an organic compound denoted by chemical formula (3) having two biphenyl derivatives linked via a double bond, the compound having diphenylamino groups (NPh$_2$) substituted for the substituents R$_1$–R$_4$ as expressed by the following chemical formula (12)

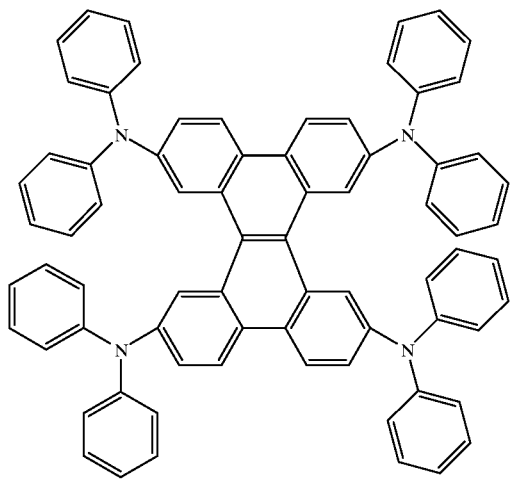

(12)

was synthesized, and used as the material for the hole transport layer of an organic EL element.

Synthesis Example 3-1

The synthesis method for the compound of the above chemical formula (12) is described according to the following chemical reaction formula (13).

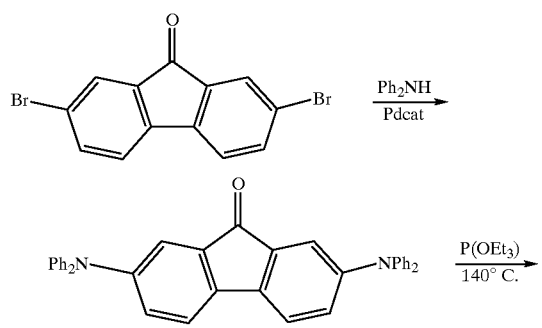

(13)

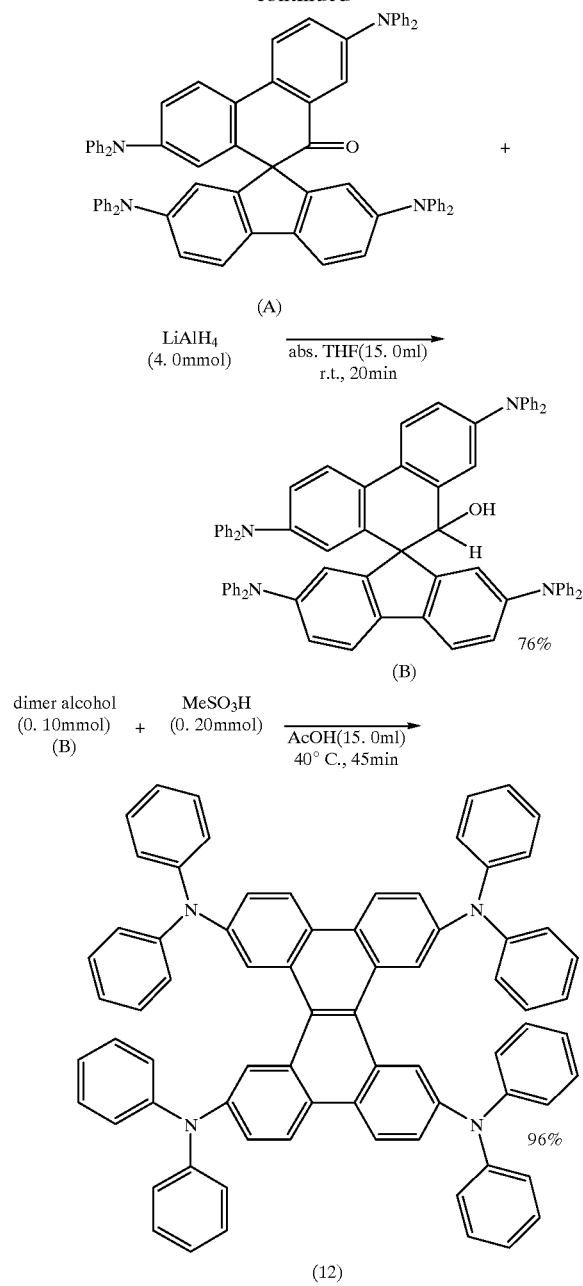

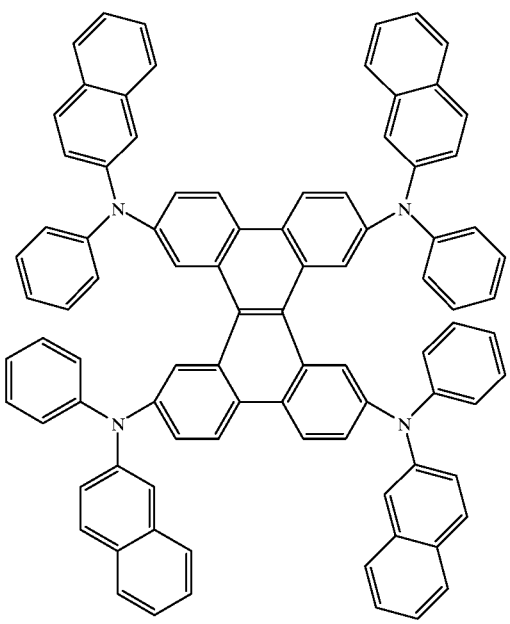

The procedure shown in the top row of reaction formula (13) was used to produce spiroketone having tetraamino group, as denoted by (A) in reaction formula (13). In anhydrous tetrahydrofuran (THF), 0.30 mmol of the spiroketone was stirred with excess (4.0 mmol) lithium aluminium hydride (LiAlH$_4$) for 20 minutes at room temperature to produce corresponding dimer alcohol denoted by (B) in reaction formula (13). The yield was 76%. Subsequently, this raw product, namely, the compound denoted by (B), was heated in acetic acid (AcOH) with a small amount of methane sulfonate (MeSO$_3$H) at 40° C. for 45 minutes. Following this procedure, the target compound denoted by chemical formula (12) was obtained at a yield of 96%. Purification of the compound of chemical formula (12) was performed by column chromatography using silica gel, and a light yellow crystal was obtained, with a yield after purification of 70%. The glass transition temperature Tg was 152° C., and the melting point was 313° C.–314° C. However, the compound demonstrated the property to melt at 186° C.–187 ° C. and subsequently crystallize. When crystallized, the compound could only be dissolved in a large amount of CHCl$_3$ or PhH, and was insoluble in acetone.

Element Production Example 3-1

The organic EL element produced using the compound of chemical formula (12) obtained according to the above Synthesis Example 3-1 has a configuration as shown in FIG. 1(c). Referring to FIG. 2, although the configuration of the organic compound layer 20 differs from that of FIG. 2, the element comprised a glass substrate 10 having an ITO layer disposed on its surface in advance to be used as the transparent electrode. In the present Example 3-1, over the transparent electrode 12, the compound of the above chemical formula (12) was used to form a film at a thickness of 600 Å to provide an emissive layer that also functions as a hole transport layer. Over this layer, Alq$_3$ was used to form the electron transport layer at a thickness of 600 Å. As a metal electrode 18, an LiF layer of 5 Å and an Al layer of 1600 Å were formed in this order over the electron transport layer.

In the obtained organic EL element, a direct current voltage was applied using the transparent electrode 12 as the anode and the metal electrode 18 as the cathode. It was confirmed that blue-green light emission (emission wavelength peak: 490 nm) generated from the compound of chemical formula (12) was obtained from 3V. An emission efficiency of 6.21 m/W (3 cd/A) was observed at the luminance of 300 cd/m$^2$. The element life under the initial condition of 300 cd/m$^2$ was 4000 hours. An element having a long element life was thus achieved.

Example 3-2

Example 3-2 related to the above Embodiment 3 will now be explained. In Example 3-2, as an organic compound denoted by chemical formula (3) having two biphenyl derivatives linked via a double bond, the compound having naphthyl groups substituted for the substituents R$_1$–R$_4$ as expressed by the following chemical formula (14)

(14)

was synthesized, and used as the material for an emissive layer having hole transport property in an organic EL element.

Synthesis Example 3-2

The synthesis method for the compound of the above chemical formula (14) is described according to the following chemical reaction formula (15).

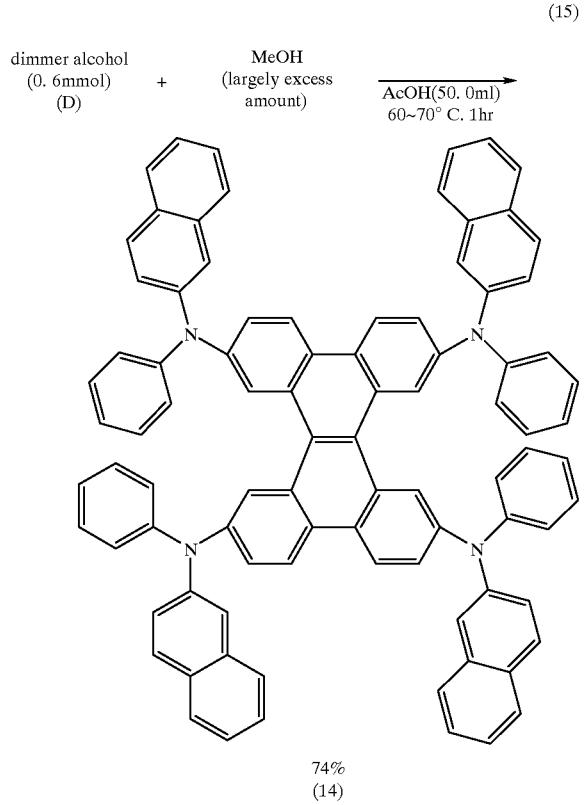

(15)

dimmer alcohol (0. 6mmol) (D) + MeOH (largely excess amount) → AcOH(50. 0ml) 60~70° C. 1hr

74%
(14)

The compound denoted by chemical formula (14) was produced using a compound obtained by substituting a naphthyl group for one phenyl group within a diphenylamino group of the spiroketone denoted by (A) in the above reaction formula (13). This compound was reacted in the manner shown in the middle row of reaction formula (13) to obtain the compound (D) (in reaction formula (15)) which corresponds to the dimer alcohol (B).

Subsequently, 0.6 mmol of the dimer alcohol denoted by (D) in reaction formula (15) was heated in acetic acid (AcOH) with a small, but largely excess, amount of methanol (MeOH) at 60° C.–70° C. for one hour. Following this procedure, the target compound expressed by chemical formula (14) was obtained at a yield of 74%. The obtained chemical compound was an yellow crystal having the glass transition temperature Tg of 154° C. and the melting point of 199° C.–204° C. Differing from the above chemical formula (12), the compound (14) of Example 3-2 displayed no crystallization after melting at 199° C.–204° C.

Element Production Example 3-2

The organic EL element produced using the compound of chemical formula (14) obtained according to the above Synthesis Example 3-2 had a configuration as shown in FIG. 1(c), similarly as the above Example 3-1. Referring to FIG. 2, although the configuration of the organic compound layer 20 differs from that of FIG. 2, the element comprised a glass substrate 10 having an ITO layer disposed on its surface in advance to be used as the transparent electrode. Over the transparent electrode 12, the compound of the above chemical formula (14) was used to form a film at a thickness of 600 Å to provide an emissive layer that also functions as a hole transport layer. Over this layer, an electron transport layer composed of $Alq_3$ was formed at a thickness of 600 Å. As a metal electrode 18, an LiF layer of 5 Å and an Al layer of 1600 Å were formed in this order over the electron transport layer.

In the obtained organic EL element, a direct current voltage was applied between the transparent electrode 12 and the metal electrode 18. It was confirmed that blue-green light emission (emission wavelength peak: 490 nm) generated from the compound of chemical formula (14) was obtained from 3V. Emission efficiency of 6.01 m/W could be accomplished at 300 $cd/m^2$. The element life under the initial condition of 300 $cd/m^2$ was a relatively very long 6000 hours.

Example 3-3

In Example 3-3, the compound expressed by chemical formula (14), which was obtained through the above Synthesis Example 3-2, was used to produce an organic EL element having the configuration shown in FIG. 1(c), in the same manner as in Example 3-2. The element comprised a glass substrate having an ITO layer disposed on its surface in advance to be used as the transparent electrode. Over the transparent electrode, the compound of the above chemical formula (14) was used as an emissive material having hole transport property to form a film at a thickness of 600 Å, so as to provide an emissive layer that simultaneously functions as a hole transport layer. Subsequently, over this layer, a material of oxadiazole class denoted by the following chemical formula (16)

(16)

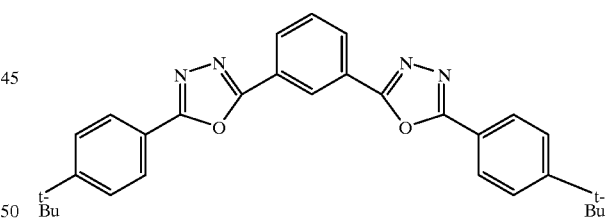

was used as the electron transport material to form an electron transport layer at a thickness of 600 Å. As a metal electrode, an LiF layer of 5 Å and an Al layer of 1600 Å were formed in this order over the electron transport layer.

In the obtained organic EL element, a direct current voltage was applied between the transparent electrode and the metal electrode. Light emission was observed from 4V, and a blue-green emission spectrum having the peak wavelength of approximately 490 nm was generated. Emission efficiency of 3 cd/A could be accomplished at the luminance of 300 $cd/m^2$. The element life under the initial condition of 300 $cd/m^2$ was 500 hours. From these results, it was found that the compound of chemical formula (14) can be used not only as a hole transport material, but also as an emissive material.

(Summary on Performance of Example 1, Example 3-1, and Example 3-2)

Table 2 shows characteristics of the element configuration 1 created in Example 1, the element configuration 3-1 created in Example 3-1, the element configuration 3-2 created in Example 3-2, and the element created in Comparison Example 1.

TABLE 2

| Material | | Emission Wavelength Peak (nm) | Emission Efficiency (1 m/W) | Half Decay Lifetime (hr) |
| --- | --- | --- | --- | --- |
| Ex 1 | chemical formula (6) | 545 | 3.5 | 5000 |
| Ex 3-1 | chemical formula (12) | 490 | 6.2 | 4000 |
| Ex 3-2 | chemical formula (14) | 490 | 6.0 | 6000 |
| Comp 1 | α-NPD | 530 | 5.0 | 3000 |

In Example 1 (Ex 1), Example 3-1 (Ex 3-1), and Example 3-2 (Ex 3-2), the organic compounds of chemical formulas (6), (12), and (14) were used, respectively, as the emissive layer having hole transport property, and diphenylamino groups were introduced as the substituents $R_1$–$R_4$. The element of Comparison Example 1 employed α-NPD as the hole transport layer, and $Alq_3$ as the emissive layer. The emitted colors of the elements of the Examples were yellow, blue-green, and blue-green, in order from the top of the Table, while the element of the Comparison Example demonstrated green light emission. Accordingly, it can be inferred that, in the Example elements, the obtained light was generated from the compounds of the respective chemical formulas (6), (12), and (14), rather than from $Alq_3$ which was used for the electron transport layer. The emission efficiency of the element of Example 1 did not reach the level of Comparison Example 1, but very high efficiency could be accomplished in Example 3-1 and Example 3-2. Whereas the luminance half decay lifetime of the element was about 3000 hours in Comparison Example 1, the values for the elements of Examples 1, 3-1, and 3-2 were 5000 hours, 4000 hours, and 6000 hours, respectively, showing that bright and stable elements could be achieved.

Example 3-4

In this Example 3-4, the compound of chemical formula (12) obtained through the above Synthesis Example 3-1 was used as the host material of the emissive layer. As the doping material, quinacrydone denoted by the following chemical formula (17) was used.

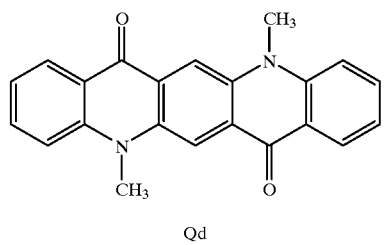

(17)

Qd

In the same manner as in the above Examples, such as Example 3-1, the organic EL element was created using a glass substrate 10 having an ITO layer disposed on its surface in advance to be used as the transparent electrode 12. In the present Example 3-4, an emissive layer was formed on the substrate 10 by first disposing the compound of chemical formula (12) at a thickness of 400 Å, then, over this layer, carefully depositing (while observing through a deposition monitor) quinacrydone expressed by the above chemical formula (17) such that the ratio (volume ratio) of the compound of chemical formula (12) to quinacrydone becomes 100:1. Subsequently, $Alq_3$ was formed at a thickness of 600 Å as the electron transport layer. Over the electron transport layer, an LiF layer of 5 Å and an Al layer of 1600 Å were formed, in that order, to provide a cathode.

When the obtained element was operated, the emitted color of the element was green, indicating that the light emission was generated from quinacrydone. The emission efficiency was 10 cd/A. It is understood that the element emission efficiency was remarkably enhanced, especially in comparison with the element created in Example 3-1 (Production Example 3-1) in which the efficiency was 3 cd/A. The emission luminance half decay lifetime at 300 cd/m² was approximately 5000 hours. An element having high luminance and excellent stability was thus obtained.

Example 3-5

In Example 3-5, a first emissive layer was formed using the compound obtained in the above Synthesis Example 3-1 denoted by chemical formula (12), and a second emissive layer was formed using another material. By allowing lights generated from both of these emissive layers to coexist, a mixed color was obtained. In this example, the emitted light was observed to be white.

Figure 8:
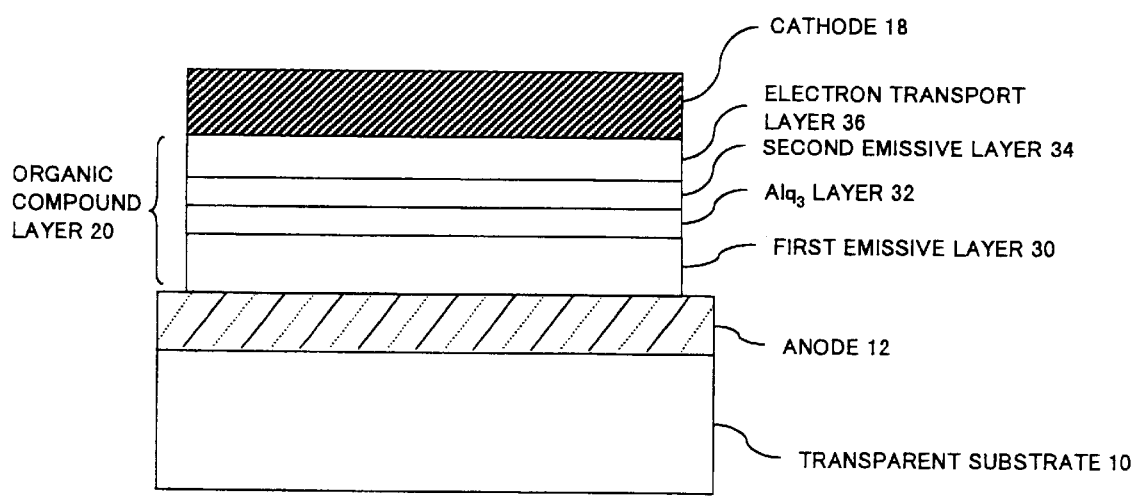
FIG. 8 is a schematic cross-sectional view showing the configuration of the organic EL elements according to Examples 3–5.

FIG. 8 shows the configuration of the element according to the present Example 3-5. As shown, the organic EL element employed a transparent substrate (glass substrate) 10 having an ITO layer disposed on its surface in advance to be used as the transparent electrode 12, as in the above-described examples such as Example 3-1. On this substrate 10, the compound of chemical formula (12) was first formed at a thickness of 500 Å to provide the first emissive layer 30. Over the first emissive layer 30, $Alq_3$ layer 32 was disposed at a thickness of 200 Å so as to prevent energy movement from the first emissive layer 30 to the second emissive layer 34. Subsequently, the second emissive layer 34 was formed at a thickness of 200 Å using $Alq_3$ as the host material, and the compound (DCM1) denoted by the following chemical formula (18) as the doping material.

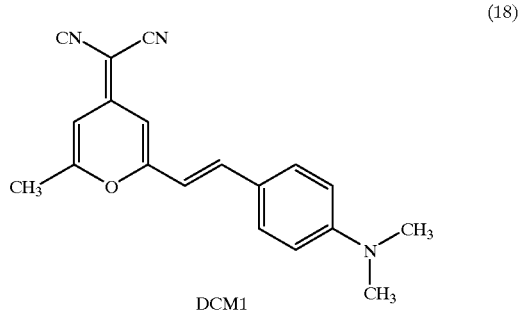

(18)

DCM1

An electron transport layer 36 was then formed over the second emissive layer 34 at a thickness of 300 Å using $Alq_3$. As the cathode 18, an LiF layer of 5 Å and an Al layer of 1600 Å were formed in this order over the electron transport layer 36.

When the created element was operated, the peak wavelengths of the emitted light were observed at 490 nm and 600 nm. Overall, a white light emission having a broad peak range (half-value range 150 nm) was generated. This white light emission was obtained by mixing lights generated from the compound of chemical formula (12) in the first emissive layer 30 and from DCM1 in the second emissive layer 34.

Example 4

In this element, a maximum emission luminance of 10000 cd/m² could be accomplished. An organic EL element emitting bright white light could thus be obtained.

Example 4 related to the above Embodiment 4 will next be explained. In Example 4, as an organic compound usable for the organic compound layer of an organic EL element, the compound of the following chemical formula (19)

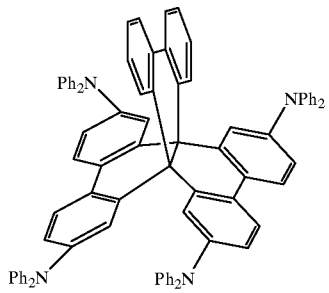
(19)

was synthesized as one example of a biphenyl derivative having a three-dimensional structure expressed by chemical formula (4). The compound of chemical formula (19) can be described as chemical formula (1) with a biphenyl group introduced in the position of [A], and has a three-dimensional structure.

The synthesis method for the compound of chemical formula (19) is described below according to the following chemical reaction formula (20).

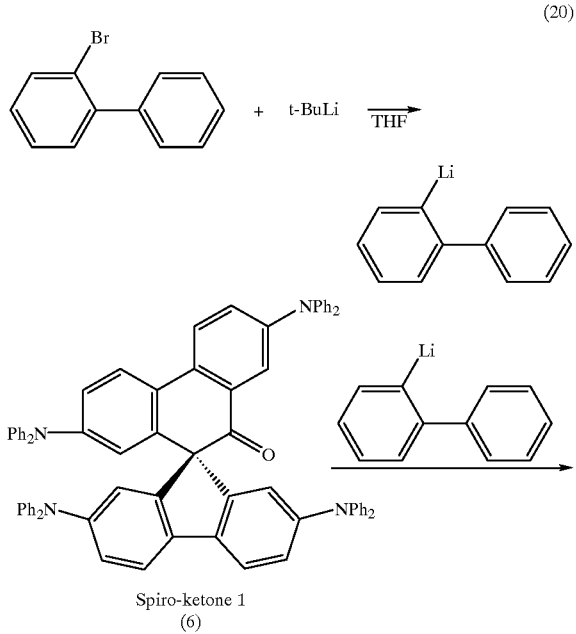
(20)

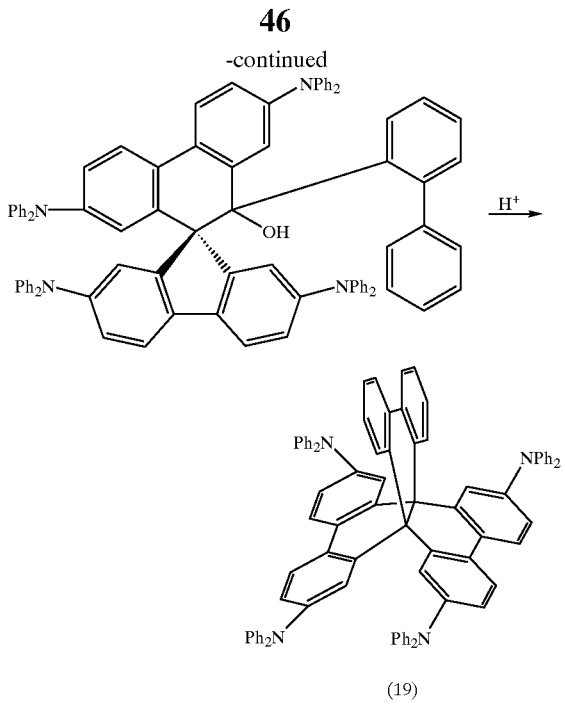
(19)

First, as indicated in the upper row of formula (20), o-bromobiphenyl (1.5 mmol) was lithiated (Li) using t-BuLi (4.0 mmol) in THF. Subsequently, as shown in the lower row of formula (20), the lithiated biphenyl was dropped into THF solution of spiroketone (1.13 mmol) which corresponds to the above chemical formula (6). During this procedure, the solution was refluxed and stirred for 1.5 days. The solution was then neutralized. The reacted matter was hydrolized, and the obtained reacted matter was purified to produced the target compound denoted by chemical formula (19). When the reacted matter after hydrolysis was examined by high performance liquid chromatography (HPLC) and TLC, the peaks corresponding to the raw materials were no longer observed, and it was evidenced that the compound of chemical formula (19) was obtained.

Due to its three-dimensional structure, the compound denoted by chemical formula (19) produced in this way has a high glass transition temperature Tg and also a high melting point. Accordingly, production of organic EL elements using a compound as expressed by chemical formula (19) contributes to enhancement of element heat resistance.

INDUSTRIAL APPLICABILITY

The above-described organic EL elements can be used in a backlight of a planar light source such as a liquid crystal display. Alternatively, the organic EL elements can be used directly as a planar display.

What is claimed is:
1. An organic electroluminescence element comprising an anode, a cathode, and one or more organic compound layers sandwiched between the anode and cathode, wherein at least one layer of said organic compound layers comprises an organic compound denoted by the following chemical formula

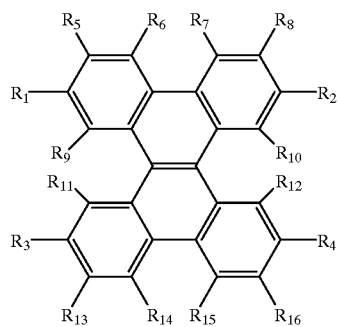

wherein $R_1$–$R_{16}$ are independently selected from the group consisting of hydrogen, an alkyl group, an alkoxy group, a phenyl group, a substituted phenyl group, a diphenylamino group, a diarylamino group, a heterocyclic group and a substituted heterocyclic group.

2. The organic electroluminescence element defined in claim 1, wherein said organic compound denoted by formula 3 functions as an electron transport material.

3. The organic electroluminescence element defined in claim 1, wherein the organic compound denoted by formula 3 functions as a hole transport material.

4. The organic electroluminescence element defined in claim 1, wherein the organic compound denoted by formula 3 functions as an emissive layer material having hole transport function.

5. The organic electroluminescence element defined in claim 1, wherein the organic compound denoted by formula 3 functions as a host material in an emissive layer constituted by injecting a doping material into the host material.

6. The organic electroluminescence element defined in claim 1 further, comprising:

a first emissive layer including, as an emissive material, an organic compound denoted by formula 3; and a second emissive layer including a material differing from a material included in the first emissive layer; wherein light emitted by the element is mixed light of light from said first emissive layer and light from said second emissive layer.

7. The organic electroluminescence element as claimed in claim 1, wherein said at least one layer of said organic compound layers comprises an organic compound denoted by the following chemical formula:

8. The organic electroluminescence element as claimed in claim 1, wherein said at least one layer of said organic compound layers comprises an organic compound denoted by the following chemical formula:

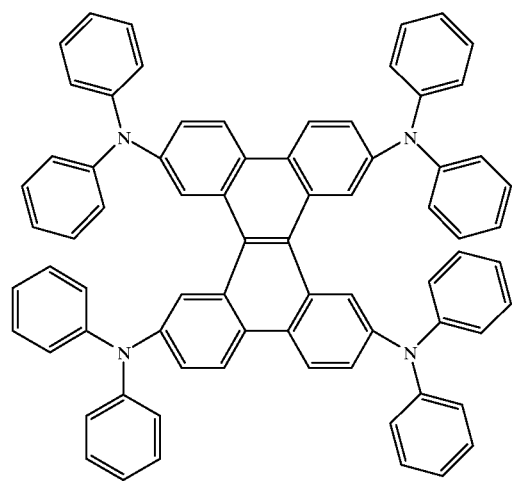

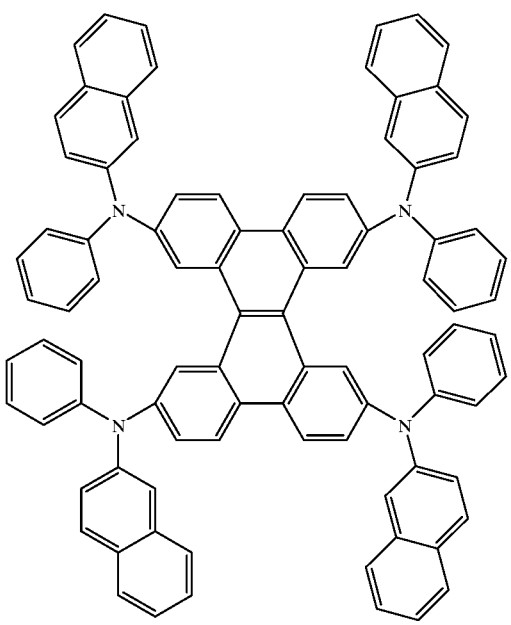

* * * * *

UNITED STATES PATENT AND TRADEMARK OFFICE
CERTIFICATE OF CORRECTION

PATENT NO. : 6,416,887 B1
DATED : July 9, 2002
INVENTOR(S) : Tokito et al.

It is certified that error appears in the above-identified patent and that said Letters Patent is hereby corrected as shown below:

<u>Title page,</u>
Item [30], Foreign Application Priority Data, should read:

--      Foreign Application Priority Data
Nov. 11, 1998   (JP)  …………………….. 10-321080
Mar. 11, 1999   (JP)  …………………….11-65683 --

Signed and Sealed this

Twenty-eighth Day of January, 2003

JAMES E. ROGAN
*Director of the United States Patent and Trademark Office*